US010368559B2

(12) United States Patent
Horvath et al.

(10) Patent No.: US 10,368,559 B2
(45) Date of Patent: Aug. 6, 2019

(54) STREPTOCOCCUS THERMOPHILUS STRAINS

(71) Applicant: DUPONT NUTRITION BIOSCIENCES APS, Copenhagen K (DK)

(72) Inventors: Philippe Horvath, Châtellerault (FR); Christophe Fremaux, Poitiers (FR); Pascal Fourcassie, Poitiers (FR)

(73) Assignee: DuPont Nutrition Biosciences ApS (DK)

( * ) Notice: Subject to any disclaimer, the term of this patent is extended or adjusted under 35 U.S.C. 154(b) by 445 days.

(21) Appl. No.: 14/905,125

(22) PCT Filed: Jul. 16, 2014

(86) PCT No.: PCT/EP2014/065286
§ 371 (c)(1),
(2) Date: Jan. 14, 2016

(87) PCT Pub. No.: WO2015/007791
PCT Pub. Date: Jan. 22, 2015

(65) Prior Publication Data
US 2016/0165910 A1    Jun. 16, 2016

(30) Foreign Application Priority Data
Jul. 17, 2013  (EP) .................................. 13176911

(51) Int. Cl.
| A23C 9/123 | (2006.01) |
| A23C 9/127 | (2006.01) |
| A23C 19/032 | (2006.01) |
| A23C 21/02 | (2006.01) |
| C12N 1/20 | (2006.01) |
| A23L 33/135 | (2016.01) |
| C12R 1/46 | (2006.01) |

(52) U.S. Cl.
CPC ............ *A23C 9/1238* (2013.01); *A23C 9/127* (2013.01); *A23C 19/032* (2013.01); *A23C 21/02* (2013.01); *A23L 33/135* (2016.08); *C12N 1/20* (2013.01); *C12R 1/46* (2013.01); *A23V 2002/00* (2013.01); *A23Y 2240/75* (2013.01)

(58) Field of Classification Search
CPC ...... C12N 15/52; C12N 15/74; C12N 9/1007; C12N 15/67; C12N 15/8245; C12N 15/87; C12N 9/2465; C12P 7/6409; C12P 7/6436; C12P 7/6463; C12P 7/649; C12Y 111/01006; Y02E 50/13; Y02P 60/247; A23V 2002/00
See application file for complete search history.

(56) References Cited

U.S. PATENT DOCUMENTS
8,198,065 B2   6/2012  Druesne et al.
2009/0304864 A1  12/2009  Marchal et al.

FOREIGN PATENT DOCUMENTS
| EP | 2437611 B1 | 11/2016 |
| FR | 2629612 A1 | 10/1989 |
| WO | 2006/128864 A2 | 12/2006 |
| WO | 2007/077401 A2 | 7/2007 |
| WO | 2007/136815 A2 | 11/2007 |
| WO | 2008/108989 A2 | 9/2008 |

OTHER PUBLICATIONS

Barrangou et al., "CRISPR provides acquired resistance against viruses in prokaryotes", Science, vol. 315, No. 5819 (2007) pp. 1709-1712.
Bolotin et al., "Clustered regularly interspaced short palindrome repeats (CRISPRs) have spacers of extrachromosomal origin", Microbiology, vol. 151, No. Pt 8, (2005) pp. 2551-2561.
Corrieu et al., "CINAC, Automated Lactic Starter Monitoring and Characterization System", Process Magazine (1992) 1068, pp. 24-27.
Jansen et al., "Identification of a Novel Family of Sequence repeats among Prokaryotes" OMICS A Journal of Integrative Biology, vol. 6, No. 1 (2002).
Sapranauskas et al., "The *Streptococcus thermophilus* CRISPR/Cas system provides immunity in *Escherichia coli*", Nucleic Acids Research, (2011) vol. 39, No. 21, pp. 9275-9282.
International Search Report for International Application No. PCT/EP20141065286, dated Oct. 13, 2014, European Patent Office, P.B. 5818 Patentlaan 2, NL-2280 HV Rijswijk, Jacqueline Van Ekelenburg, Authorized Office.
Extended European Search Report for application No. 13176911. 9-14091, dated Nov. 29, 2013, the Hague.
Delorme et al., "Emergence of a Cell Wall Protease in the *Streptococcus thermophilus* Population", Applied and Enviromental Micro, vol. 76, No. 2, pp. 451-460, Jan. 2010.

*Primary Examiner* — Deborah K Ware

(57) ABSTRACT

The present invention relates to *Streptococcus thermophilus* strains, usable as starter cultures, able to provide both satisfactory rheological and organoleptic properties, and satisfactory shelf life to the media into which they are incorporated. In particular, these strains are also bacteriophage-resistant, thereby minimizing bacteriophage infection. The invention also provides a composition comprising one of these *Streptococcus thermophilus* strains, and feed or food products obtained with these strains.

34 Claims, 2 Drawing Sheets
Specification includes a Sequence Listing.

A.

B.

SEQUENCE LISTING

```
<160> NUMBER OF SEQ ID NOS: 103

<210> SEQ ID NO 1
<211> LENGTH: 20
<212> TYPE: DNA
<213> ORGANISM: Streptococcus thermophilus

<400> SEQUENCE: 1
ttccattggg atcttttagt                                              20

<210> SEQ ID NO 2
<211> LENGTH: 257
<212> TYPE: DNA
<213> ORGANISM: Streptococcus thermophilus

<400> SEQUENCE: 2
acaaatttag gtcatatgga gatacgacaa tatcaatcga ttggttgagg tctcttttta   60
gatttgttaa ttagttgatt acttttttaag tattgccgtt gtaagcagca tatcttaaag  120
atagagatgc tgtaaaactt tctcatagac tactacatat tgttttagag ctatgttttt  180
tctaatggtt ccaaaacaat cgctttctct ttatatgccc accaaaaaaa agccagtggc  240 tcttttaaa tatcatc                                                  257

<210> SEQ ID NO 3
<211> LENGTH: 763
<212> TYPE: DNA
<213> ORGANISM: Streptococcus thermophilus

<400> SEQUENCE: 3 gttttcccg cacacgcggg ggtgatccta tacctatatc aatggcctcc cacgcataag    60 cgttttccc gcacacgcgg gggtgatccc gacaccacta gggcgagtct gagcgccccc   120 aggttttcc cgcacacgcg ggggtgatcc cgcaacccct ccttagacat gggaacagta   180 ctagttttc ccgcacacgc gggggtgatc cctgtattat cggcgaatag atcagattct   240
```

```
tctggttttt cccgcacacg cgggggtgat ccacccttac aaggctgata gacctttgtc    300 gtttggttttt tcccgcacac gcgggggtga tccctcgttt aaatttgtag ttatcattaa    360
caatatgttt ttcccgcaca cgcgggggtg atcccaaggt aaaattgccg acaatgttgg    420
aacgttggtt tttcccgcac acgcgggggt gatcctatac attacctcat ttccagctga    480
gaacattggt ttttcccgca cacgcggggg tgatcctcag cgcctcgaca agcatcaaga    540
agaacagaag tttttcccgc acacgcgggg gtgatcctgt actggttgag tattcaaggt    600
aggtgtgcca cgttttttccc gcacacgcgg gggtgatcca tactcaactt ccttacccctt    660 aaccccttttc aaagttttttc ccgcacacgc ggggtgatc ctggtcgtgt gtttggcatt    720
ggctcaatgg gaacagttttt tcccgcacac gcggggtga ttc    763
```

<210> SEQ ID NO 4
<211> LENGTH: 61
<212> TYPE: DNA
<213> ORGANISM: Streptococcus thermophilus

<400> SEQUENCE: 4

```
gttttttcccg cacacgcggg ggtgatccta tacctatatc aatggcctcc cacgcataag    60
c                                                                    61
```

<210> SEQ ID NO 5
<211> LENGTH: 61
<212> TYPE: DNA
<213> ORGANISM: Streptococcus thermophilus

<400> SEQUENCE: 5

```
gttttttcccg cacacgcggg ggtgatcccg acaccactag ggcgagtctg agcgccccca    60
g                                                                    61
```

<210> SEQ ID NO 6
<211> LENGTH: 61
<212> TYPE: DNA
<213> ORGANISM: Streptococcus thermophilus

<400> SEQUENCE: 6

```
gttttttcccg cacacgcggg ggtgatcccg caaccccctcc ttagacatgg gaacagtact    60
a                                                                    61
```

<210> SEQ ID NO 7
<211> LENGTH: 61
<212> TYPE: DNA
<213> ORGANISM: Streptococcus thermophilus

<400> SEQUENCE: 7

```
gttttttcccg cacacgcggg ggtgatccct gtattatcgg cgaatagatc agattcttct    60
g                                                                    61
```

<210> SEQ ID NO 8
<211> LENGTH: 61
<212> TYPE: DNA
<213> ORGANISM: Streptococcus thermophilus

<400> SEQUENCE: 8

```
gttttttcccg cacacgcggg ggtgatccac ccttacaagg ctgatagacc tttgtcgttt    60
g                                                                    61
```

<210> SEQ ID NO 9
<211> LENGTH: 61
<212> TYPE: DNA
<213> ORGANISM: Streptococcus thermophilus

<400> SEQUENCE: 9
gtttttcccg cacacgcggg ggtgatccct cgtttaaatt tgtagttatc attaacaata    60
t                                                                    61

<210> SEQ ID NO 10
<211> LENGTH: 61
<212> TYPE: DNA
<213> ORGANISM: Streptococcus thermophilus

<400> SEQUENCE: 10
gtttttcccg cacacgcggg ggtgatccca aggtaaaatt gccgacaatg ttggaacgtt    60
g                                                                    61

<210> SEQ ID NO 11
<211> LENGTH: 61
<212> TYPE: DNA
<213> ORGANISM: Streptococcus thermophilus

<400> SEQUENCE: 11
gtttttcccg cacacgcggg ggtgatccta tacattacct catttccagc tgagaacatt    60
g                                                                    61

<210> SEQ ID NO 12
<211> LENGTH: 61
<212> TYPE: DNA
<213> ORGANISM: Streptococcus thermophilus

<400> SEQUENCE: 12
gtttttcccg cacacgcggg ggtgatcctc agcgcctcga caagcatcaa gaagaacaga    60
a                                                                    61

<210> SEQ ID NO 13
<211> LENGTH: 62
<212> TYPE: DNA
<213> ORGANISM: Streptococcus thermophilus

<400> SEQUENCE: 13
gtttttcccg cacacgcggg ggtgatcctg tactggttga gtattcaagg taggtgtgcc    60
ac                                                                   62

<210> SEQ ID NO 14
<211> LENGTH: 62
<212> TYPE: DNA
<213> ORGANISM: Streptococcus thermophilus

<400> SEQUENCE: 14
gtttttcccg cacacgcggg ggtgatccat actcaacttc cttaccctta acccctttca    60
aa                                                                   62

<210> SEQ ID NO 15
<211> LENGTH: 62
<212> TYPE: DNA
<213> ORGANISM: Streptococcus thermophilus

<400> SEQUENCE: 15

```
gtttttcccg cacacgcggg ggtgatcctg gtcgtgtgtt tggcattggc tcaatgggaa    60
ca                                                                    62

<210> SEQ ID NO 16
<211> LENGTH: 28
<212> TYPE: DNA
<213> ORGANISM: Streptococcus thermophilus

<400> SEQUENCE: 16
gtttttcccg cacacgcggg ggtgattc                                        28

<210> SEQ ID NO 17
<211> LENGTH: 63
<212> TYPE: DNA
<213> ORGANISM: Streptococcus thermophilus

<400> SEQUENCE: 17
caaggacagt tattgatttt ataatcacta tgtgggtata aaaacgtcaa aatttcattt    60
gag                                                                   63

<210> SEQ ID NO 18
<211> LENGTH: 41
<212> TYPE: DNA
<213> ORGANISM: Streptococcus thermophilus

<400> SEQUENCE: 18
ttgattcaac ataaaaagcc agttcaattg aacttggctt t                         41

<210> SEQ ID NO 19
<211> LENGTH: 2147
<212> TYPE: DNA
<213> ORGANISM: Streptococcus thermophilus

<400> SEQUENCE: 19 gttttttgtac tctcaagatt taagtaactg tacaactgtt tgacagcaaa tcaagattcg    60
aattgtgttt ttgtactctc aagatttaag taactgtaca acaatgacga ggagctattg   120
gcacaactta cagttttttgt actctcaaga tttaagtaac tgtacaaccg atttgacaat   180
ctgctgacca ctgttatcgt ttttgtactc tcaagattta agtaactgta caacacactt   240
ggcaggctta ttactcaaca gcgagttttt gtactctcaa gatttaagta actgtacaac   300
ctgttccttg ttcttttgtt gtatcttttc gttttttgtac tctcaagatt taagtaactg   360
tacaacttca ttcttccgtt tttgtttgcg aatcctgttt ttgtactctc aagatttaag   420
taactgtaca acgctggcga ggaaacgaac aaggcctcaa cagttttttgt actctcaaga   480 tttaagtaac tgtacaacca tagagtggaa aactagaaac agattcaagt ttttgtactc   540
tcaagattta agtaactgta caacataatg ccgttgaatt acacggcaag gtcagtttttt   600 gtactctcaa gatttaagta actgtacaac gagcgagctc gaaataatct taattacaag   660 gttttttgtac tctcaagatt taagtaactg tacaacgttc gctagcgtca tgtggtaacg   720
tatttagttt ttgtactctc aagatttaag taactgtaca acggcgtccc aatcctgatt   780
aatacttact cggttttttgt actctcaaga tttaagtaac tgtacaacaa cacagcaaga   840
caagaggatg atgctatggt ttttgtactc tcaagattta agtaactgta caaccgacac   900
aagaacgtat gcaagagttc aaggttttttg tactctcaag atttaagtaa ctgtacaaca   960
caattcttca tccggtaact gctcaagtgg tttttgtact ctcaagattt aagtaactgt  1020
```

```
acaacaatta agggcataga aagggagaca acatggtttt tgtactctca agatttaagt    1080
aactgtacaa ccgatattta aaatcatttt cataacttca tgtttttgta ctctcaagat    1140
ttaagtaact gtacaacgca gtatcagcaa gcaagctgtt agttactgtt tttgtactct    1200
caagatttaa gtaactgtac aacataaact atgaaatttt ataattttta agagttttg     1260 tactctcaag atttaagtaa ctgtacaaca ataatttatg gtatagctta atatcattgg    1320
tttttgtact ctcaagattt aagtaactgt acaactgcat cgagcacgtt cgagtttacc    1380
gtttcgtttt tgtactctca agatttaagt aactgtacaa ctctatatcg aggtcaacta    1440
acaattatgc tgttttgta ctctcaagat ttaagtaact gtacaacaat cgttcaaatt     1500
ctgttttagg tacatttgtt tttgtactct caagatttaa gtaactgtac aacaatcaat    1560
acgacaagag ttaaaatggt cttgttttg tactctcaag atttaagtaa ctgtacaacg     1620
cttagctgtc aatccacga acgtggatgg ttttgtact ctcaagattt aagtaactgt      1680
acaaccaacc aacggtaaca gctacttttt acagtgtttt tgtactctca agatttaagt    1740
aactgtacaa cataactgaa ggataggagc ttgtaaagtc tgtttttgta ctctcaagat    1800
ttaagtaact gtacaactaa tgctacatct caaaggatga tcccagagtt tttgtactct    1860
caagatttaa gtaactgtac aacaagtagt tgatgacctc tacaatggtt tatgtttttg    1920
tactctcaag atttaagtaa ctgtacaaca cctagaagca tttgagcgta tattgattgg    1980
tttttgtact ctcaagattt aagtaactgt acaacaattt tgccccttct ttgccccttg    2040
actaggtttt tgtactctca agatttaagt aactgtacaa caccattagc aatcatttgt    2100
gcccattgag tgtttttgta ctctcaagat ttaagtaact gtacagt                  2147

<210> SEQ ID NO 20
<211> LENGTH: 36
<212> TYPE: DNA
<213> ORGANISM: Streptococcus thermophilus

<400> SEQUENCE: 20 gttttttgtac tctcaagatt taagtaactg tacaac                              36

<210> SEQ ID NO 21
<211> LENGTH: 36
<212> TYPE: DNA
<213> ORGANISM: Streptococcus thermophilus

<400> SEQUENCE: 21 gttttttgtac tctcaagatt taagtaactg tacagt                              36

<210> SEQ ID NO 22
<211> LENGTH: 66
<212> TYPE: DNA
<213> ORGANISM: Streptococcus thermophilus

<400> SEQUENCE: 22 gttttttgtac tctcaagatt taagtaactg tacaactgtt tgacagcaaa tcaagattcg    60
aattgt                                                                66

<210> SEQ ID NO 23
<211> LENGTH: 66
<212> TYPE: DNA
<213> ORGANISM: Streptococcus thermophilus

<400> SEQUENCE: 23 gttttttgtac tctcaagatt taagtaactg tacaacaatg acgaggagct attggcacaa    60
```

<210> SEQ ID NO 24
<211> LENGTH: 66
<212> TYPE: DNA
<213> ORGANISM: Streptococcus thermophilus

<400> SEQUENCE: 24
gtttttgtac tctcaagatt taagtaactg tacaaccgat tgacaatct gctgaccact    60 gttatc                                                              66

<210> SEQ ID NO 25
<211> LENGTH: 66
<212> TYPE: DNA
<213> ORGANISM: Streptococcus thermophilus

<400> SEQUENCE: 25
gtttttgtac tctcaagatt taagtaactg tacaacacac ttggcaggct tattactcaa    60
cagcga                                                              66

<210> SEQ ID NO 26
<211> LENGTH: 66
<212> TYPE: DNA
<213> ORGANISM: Streptococcus thermophilus

<400> SEQUENCE: 26
gtttttgtac tctcaagatt taagtaactg tacaacctgt ccttgttct tttgttgtat    60 cttttc                                                              66

<210> SEQ ID NO 27
<211> LENGTH: 66
<212> TYPE: DNA
<213> ORGANISM: Streptococcus thermophilus

<400> SEQUENCE: 27
gtttttgtac tctcaagatt taagtaactg tacaacttca ttcttccgtt tttgtttgcg    60
aatcct                                                              66

<210> SEQ ID NO 28
<211> LENGTH: 66
<212> TYPE: DNA
<213> ORGANISM: Streptococcus thermophilus

<400> SEQUENCE: 28
gtttttgtac tctcaagatt taagtaactg tacaacgctg gcgaggaaac gaacaaggcc    60
tcaaca                                                              66

<210> SEQ ID NO 29
<211> LENGTH: 66
<212> TYPE: DNA
<213> ORGANISM: Streptococcus thermophilus

<400> SEQUENCE: 29
gtttttgtac tctcaagatt taagtaactg tacaaccata gagtggaaaa ctagaaacag    60
attcaa                                                              66

<210> SEQ ID NO 30
<211> LENGTH: 66
<212> TYPE: DNA

<213> ORGANISM: Streptococcus thermophilus

<400> SEQUENCE: 30
gtttttgtac tctcaagatt taagtaactg tacaacataa tgccgttgaa ttacacggca    60
aggtca                                                              66

<210> SEQ ID NO 31
<211> LENGTH: 66
<212> TYPE: DNA
<213> ORGANISM: Streptococcus thermophilus

<400> SEQUENCE: 31
gtttttgtac tctcaagatt taagtaactg tacaacgagc gagctcgaaa taatcttaat    60
tacaag                                                              66

<210> SEQ ID NO 32
<211> LENGTH: 66
<212> TYPE: DNA
<213> ORGANISM: Streptococcus thermophilus

<400> SEQUENCE: 32
gtttttgtac tctcaagatt taagtaactg tacaacgttc gctagcgtca tgtggtaacg    60
tattta                                                              66

<210> SEQ ID NO 33
<211> LENGTH: 66
<212> TYPE: DNA
<213> ORGANISM: Streptococcus thermophilus

<400> SEQUENCE: 33
gtttttgtac tctcaagatt taagtaactg tacaacggcg tcccaatcct gattaatact    60
tactcg                                                              66

<210> SEQ ID NO 34
<211> LENGTH: 66
<212> TYPE: DNA
<213> ORGANISM: Streptococcus thermophilus

<400> SEQUENCE: 34
gtttttgtac tctcaagatt taagtaactg tacaacaaca cagcaagaca agaggatgat    60
gctatg                                                              66

<210> SEQ ID NO 35
<211> LENGTH: 65
<212> TYPE: DNA
<213> ORGANISM: Streptococcus thermophilus

<400> SEQUENCE: 35
gtttttgtac tctcaagatt taagtaactg tacaaccgac acaagaacgt atgcaagagt    60
tcaag                                                               65

<210> SEQ ID NO 36
<211> LENGTH: 66
<212> TYPE: DNA
<213> ORGANISM: Streptococcus thermophilus

<400> SEQUENCE: 36
gtttttgtac tctcaagatt taagtaactg tacaacacaa ttcttcatcc ggtaactgct    60
caagtg                                                              66

<210> SEQ ID NO 37
<211> LENGTH: 66
<212> TYPE: DNA
<213> ORGANISM: Streptococcus thermophilus

<400> SEQUENCE: 37
gtttttgtac tctcaagatt taagtaactg tacaacaatt aagggcatag aaagggagac      60
aacatg                                                                66

<210> SEQ ID NO 38
<211> LENGTH: 66
<212> TYPE: DNA
<213> ORGANISM: Streptococcus thermophilus

<400> SEQUENCE: 38
gtttttgtac tctcaagatt taagtaactg tacaaccgat atttaaaatc attttcataa      60
cttcat                                                                66

<210> SEQ ID NO 39
<211> LENGTH: 66
<212> TYPE: DNA
<213> ORGANISM: Streptococcus thermophilus

<400> SEQUENCE: 39
gtttttgtac tctcaagatt taagtaactg tacaacgcag tatcagcaag caagctgtta      60
gttact                                                                66

<210> SEQ ID NO 40
<211> LENGTH: 66
<212> TYPE: DNA
<213> ORGANISM: Streptococcus thermophilus

<400> SEQUENCE: 40
gtttttgtac tctcaagatt taagtaactg tacaacataa actatgaaat tttataattt      60
ttaaga                                                                66

<210> SEQ ID NO 41
<211> LENGTH: 66
<212> TYPE: DNA
<213> ORGANISM: Streptococcus thermophilus

<400> SEQUENCE: 41
gtttttgtac tctcaagatt taagtaactg tacaacaata atttatggta tagcttaata      60
tcattg                                                                66

<210> SEQ ID NO 42
<211> LENGTH: 66
<212> TYPE: DNA
<213> ORGANISM: Streptococcus thermophilus

<400> SEQUENCE: 42
gtttttgtac tctcaagatt taagtaactg tacaactgca tcgagcacgt tcgagtttac      60
cgtttc                                                                66

<210> SEQ ID NO 43
<211> LENGTH: 66
<212> TYPE: DNA
<213> ORGANISM: Streptococcus thermophilus

<400> SEQUENCE: 43
gtttttgtac tctcaagatt taagtaactg tacaactcta tatcgaggtc aactaacaat    60
tatgct                                                                66

<210> SEQ ID NO 44
<211> LENGTH: 66
<212> TYPE: DNA
<213> ORGANISM: Streptococcus thermophilus

<400> SEQUENCE: 44
gtttttgtac tctcaagatt taagtaactg tacaacaatc gttcaaattc tgttttaggt    60
acattt                                                                66

<210> SEQ ID NO 45
<211> LENGTH: 66
<212> TYPE: DNA
<213> ORGANISM: Streptococcus thermophilus

<400> SEQUENCE: 45
gtttttgtac tctcaagatt taagtaactg tacaacaatc aatacgacaa gagttaaaat    60
ggtctt                                                                66

<210> SEQ ID NO 46
<211> LENGTH: 66
<212> TYPE: DNA
<213> ORGANISM: Streptococcus thermophilus

<400> SEQUENCE: 46
gtttttgtac tctcaagatt taagtaactg tacaacgctt agctgtccaa tccacgaacg    60
tggatg                                                                66

<210> SEQ ID NO 47
<211> LENGTH: 66
<212> TYPE: DNA
<213> ORGANISM: Streptococcus thermophilus

<400> SEQUENCE: 47
gtttttgtac tctcaagatt taagtaactg tacaaccaac caacggtaac agctactttt    60
tacagt                                                                66

<210> SEQ ID NO 48
<211> LENGTH: 66
<212> TYPE: DNA
<213> ORGANISM: Streptococcus thermophilus

<400> SEQUENCE: 48
gtttttgtac tctcaagatt taagtaactg tacaacataa ctgaaggata ggagcttgta    60
aagtct                                                                66

<210> SEQ ID NO 49
<211> LENGTH: 66
<212> TYPE: DNA
<213> ORGANISM: Streptococcus thermophilus

<400> SEQUENCE: 49
gtttttgtac tctcaagatt taagtaactg tacaactaat gctacatctc aaaggatgat    60
cccaga                                                                66

<210> SEQ ID NO 50
<211> LENGTH: 66
<212> TYPE: DNA
<213> ORGANISM: Streptococcus thermophilus

<400> SEQUENCE: 50
gtttttgtac tctcaagatt taagtaactg tacaacaagt agttgatgac ctctacaatg   60
gtttat                                                              66

<210> SEQ ID NO 51
<211> LENGTH: 66
<212> TYPE: DNA
<213> ORGANISM: Streptococcus thermophilus

<400> SEQUENCE: 51
gtttttgtac tctcaagatt taagtaactg tacaacacct agaagcattt gagcgtatat   60
tgattg                                                              66

<210> SEQ ID NO 52
<211> LENGTH: 66
<212> TYPE: DNA
<213> ORGANISM: Streptococcus thermophilus

<400> SEQUENCE: 52
gtttttgtac tctcaagatt taagtaactg tacaacaatt ttgccccttc tttgcccctt   60
gactag                                                              66

<210> SEQ ID NO 53
<211> LENGTH: 66
<212> TYPE: DNA
<213> ORGANISM: Streptococcus thermophilus

<400> SEQUENCE: 53
gtttttgtac tctcaagatt taagtaactg tacaacacca ttagcaatca tttgtgccca   60
ttgagt                                                              66

<210> SEQ ID NO 54
<211> LENGTH: 63
<212> TYPE: DNA
<213> ORGANISM: Streptococcus thermophilus
<220> FEATURE:
<221> NAME/KEY: misc_feature
<222> LOCATION: (37)..(63)
<223> OTHER INFORMATION: n is a, c, g, or t

<400> SEQUENCE: 54
gtttttgtac tctcaagatt taagtaactg tacaacnnnn nnnnnnnnn nnnnnnnnnn    60 nnn                                                                 63

<210> SEQ ID NO 55
<211> LENGTH: 64
<212> TYPE: DNA
<213> ORGANISM: Streptococcus thermophilus
<220> FEATURE:
<221> NAME/KEY: misc_feature
<222> LOCATION: (37)..(64)
<223> OTHER INFORMATION: n is a, c, g, or t

<400> SEQUENCE: 55
gtttttgtac tctcaagatt taagtaactg tacaacnnnn nnnnnnnnn nnnnnnnnnn    60 nnnn                                                                64

```
<210> SEQ ID NO 56
<211> LENGTH: 65
<212> TYPE: DNA
<213> ORGANISM: Streptococcus thermophilus
<220> FEATURE:
<221> NAME/KEY: misc_feature
<222> LOCATION: (37)..(65)
<223> OTHER INFORMATION: n is a, c, g, or t

<400> SEQUENCE: 56
gtttttgtac tctcaagatt taagtaactg tacaacnnnn nnnnnnnnnn nnnnnnnnn    60 nnnnn                                                              65

<210> SEQ ID NO 57
<211> LENGTH: 66
<212> TYPE: DNA
<213> ORGANISM: Streptococcus thermophilus
<220> FEATURE:
<221> NAME/KEY: misc_feature
<222> LOCATION: (37)..(66)
<223> OTHER INFORMATION: n is a, c, g, or t

<400> SEQUENCE: 57
gtttttgtac tctcaagatt taagtaactg tacaacnnnn nnnnnnnnnn nnnnnnnnn    60 nnnnnn                                                             66

<210> SEQ ID NO 58
<211> LENGTH: 67
<212> TYPE: DNA
<213> ORGANISM: Streptococcus thermophilus
<220> FEATURE:
<221> NAME/KEY: misc_feature
<222> LOCATION: (37)..(67)
<223> OTHER INFORMATION: n is a, c, g, or t

<400> SEQUENCE: 58
gtttttgtac tctcaagatt taagtaactg tacaacnnnn nnnnnnnnnn nnnnnnnnn    60 nnnnnnn                                                            67

<210> SEQ ID NO 59
<211> LENGTH: 68
<212> TYPE: DNA
<213> ORGANISM: Streptococcus thermophilus
<220> FEATURE:
<221> NAME/KEY: misc_feature
<222> LOCATION: (37)..(68)
<223> OTHER INFORMATION: n is a, c, g, or t

<400> SEQUENCE: 59
gtttttgtac tctcaagatt taagtaactg tacaacnnnn nnnnnnnnnn nnnnnnnnn    60 nnnnnnnn                                                           68

<210> SEQ ID NO 60
<211> LENGTH: 69
<212> TYPE: DNA
<213> ORGANISM: Streptococcus thermophilus
<220> FEATURE:
<221> NAME/KEY: misc_feature
<222> LOCATION: (37)..(69)
<223> OTHER INFORMATION: n is a, c, g, or t

<400> SEQUENCE: 60
gtttttgtac tctcaagatt taagtaactg tacaacnnnn nnnnnnnnnn nnnnnnnnn    60 nnnnnnnnn                                                          69
```

```
<210> SEQ ID NO 61
<211> LENGTH: 66
<212> TYPE: DNA
<213> ORGANISM: Streptococcus thermophilus

<400> SEQUENCE: 61 gttttgtac tctcaagatt taagtaactg tacaaccaac acattcaaca gattaatgaa      60
gaatac                                                                66

<210> SEQ ID NO 62
<211> LENGTH: 66
<212> TYPE: DNA
<213> ORGANISM: Streptococcus thermophilus

<400> SEQUENCE: 62 gttttgtac tctcaagatt taagtaactg tacaactcca ctcacgtaca aatagtgagt      60
gtactc                                                                66

<210> SEQ ID NO 63
<211> LENGTH: 66
<212> TYPE: DNA
<213> ORGANISM: Streptococcus thermophilus

<400> SEQUENCE: 63 gttttgtac tctcaagatt taagtaactg tacaacaaat cagttttttg ttcagaaact      60
tgttct                                                                66

<210> SEQ ID NO 64
<211> LENGTH: 66
<212> TYPE: DNA
<213> ORGANISM: Streptococcus thermophilus

<400> SEQUENCE: 64 gttttgtac tctcaagatt taagtaactg tacaaccagc ttgaaatgtt tattgaagca      60
gcagtg                                                                66

<210> SEQ ID NO 65
<211> LENGTH: 66
<212> TYPE: DNA
<213> ORGANISM: Streptococcus thermophilus

<400> SEQUENCE: 65 gttttgtac tctcaagatt taagtaactg tacaacgccc ttctaattgg attaccttcc      60
gaggtg                                                                66

<210> SEQ ID NO 66
<211> LENGTH: 66
<212> TYPE: DNA
<213> ORGANISM: Streptococcus thermophilus

<400> SEQUENCE: 66 gttttgtac tctcaagatt taagtaactg tacaacttat atcgaagaac gactgaaaga      60
gcttga                                                                66

<210> SEQ ID NO 67
<211> LENGTH: 65
<212> TYPE: DNA
<213> ORGANISM: Streptococcus thermophilus
```

-continued

<400> SEQUENCE: 67
gtttttgtac tctcaagatt taagtaactg tacaacctgg aaagcatatt gagggagcta     60
ctctt                                                                65

<210> SEQ ID NO 68
<211> LENGTH: 66
<212> TYPE: DNA
<213> ORGANISM: Streptococcus thermophilus

<400> SEQUENCE: 68
gtttttgtac tctcaagatt taagtaactg tacaactcta atcccactag gaatagtggg     60
tagtaa                                                                66

<210> SEQ ID NO 69
<211> LENGTH: 66
<212> TYPE: DNA
<213> ORGANISM: Streptococcus thermophilus

<400> SEQUENCE: 69
gtttttgtac tctcaagatt taagtaactg tacaacctca gtcgttactg gtgaaccagt     60
ttcaat                                                                66

<210> SEQ ID NO 70
<211> LENGTH: 66
<212> TYPE: DNA
<213> ORGANISM: Streptococcus thermophilus

<400> SEQUENCE: 70
gtttttgtac tctcaagatt taagtaactg tacaacaagc agaaaagaaa tattttggta     60
agtatg                                                                66

<210> SEQ ID NO 71
<211> LENGTH: 321
<212> TYPE: DNA
<213> ORGANISM: Streptococcus thermophilus

<400> SEQUENCE: 71
taaattagta ataagtatag atagtcttga gttatttcaa gactatcttt tagtatttag     60
tagtttctgt atgaagttga atgggataat cattttgtta gagagtagat tataaggatt    120
tgatagagga ggaattaagt tgcttgacat atgattatta agaaataatc taatatggtg    180
acagtcacat cttgtctaaa acgttgatat ataaggattt ttaaggtata ataaatataa    240
aattggaatt attttgaagc tgaagtcatg ctgagattaa tagtgcgatt acgaaatctg    300
gtagaaaaga tatcctacga g                                              321

<210> SEQ ID NO 72
<211> LENGTH: 83
<212> TYPE: DNA
<213> ORGANISM: Streptococcus thermophilus

<400> SEQUENCE: 72
ttttgttatc acaattttcg gttgacatct cttagaactc atcttatcat aaaggagtct     60
agtattaaaa tatgagaagg aac                                             83

<210> SEQ ID NO 73
<211> LENGTH: 828
<212> TYPE: DNA
<213> ORGANISM: Streptococcus thermophilus

<400> SEQUENCE: 73

```
gttttagagc tgtgttgttt cgaatggttc caaaacaaat tctaaacgct aaagaggaag      60
aggacagttt tagagctgtg ttgtttcgaa tggttccaaa actactgctg tattagcttg     120
gttgttggtt tggttttaga gctgtgttgt ttcgaatggt tccaaaactt cctcttgtaa     180 acatttatt aataatgtgt tttagagctg tgttgtttcg aatggttcca aaactatccc     240
agagaatgga agaacaatta tagagtttta gagctgtgtt gtttcgaatg gttccaaaac     300
tatgaattgt caaattaacg gttgcgctaa gttttagagc tgtgttgttt cgaatggttc     360
caaaaccgat ggaaatgatg gcttgccagg taaggagttt tagagctgtg ttgtttcgaa     420
tggttccaaa acaatgggaa agtagctata tatgatccag aggttttaga gctgtgttgt     480
ttcgaatggt tccaaaacga aggcacaaga aagtcaaatg cgtagcgcgt tttagagctg     540
tgttgtttcg aatggttcca aaacaatttt aacagatata gtgtaatcgg tattgtttta     600
gagctgtgtt gtttcgaatg gttccaaaac ctattactat acttccgaag agattgcaga     660
gttttagagc tgtgttgttt cgaatggttc caaaactatc ccagagaatg gaagaacaat     720
tatagagttt tagagctgtg ttgtttcgaa tggttccaaa actatgaatt gtcaaattaa     780
cggttgcgct aagttttaga gctgtgttgt ttcgaatggt tccaaaac                 828
```

```
<210> SEQ ID NO 74
<211> LENGTH: 36
<212> TYPE: DNA
<213> ORGANISM: Streptococcus thermophilus
```

<400> SEQUENCE: 74

```
gttttagagc tgtgttgttt cgaatggttc caaaac                                36
```

```
<210> SEQ ID NO 75
<211> LENGTH: 66
<212> TYPE: DNA
<213> ORGANISM: Streptococcus thermophilus
```

<400> SEQUENCE: 75

```
gttttagagc tgtgttgttt cgaatggttc caaaacaaat tctaaacgct aaagaggaag      60
aggaca                                                                66
```

```
<210> SEQ ID NO 76
<211> LENGTH: 66
<212> TYPE: DNA
<213> ORGANISM: Streptococcus thermophilus
```

<400> SEQUENCE: 76

```
gttttagagc tgtgttgttt cgaatggttc caaaactact gctgtattag cttggttgtt      60
ggtttg                                                                66
```

```
<210> SEQ ID NO 77
<211> LENGTH: 66
<212> TYPE: DNA
<213> ORGANISM: Streptococcus thermophilus
```

<400> SEQUENCE: 77

```
gttttagagc tgtgttgttt cgaatggttc caaaacttcc tcttgtaaac attttattaa      60
taatgt                                                                66
```

```
<210> SEQ ID NO 78
```

```
<211> LENGTH: 66
<212> TYPE: DNA
<213> ORGANISM: Streptococcus thermophilus

<400> SEQUENCE: 78
gttttagagc tgtgttgttt cgaatggttc caaaactatc ccagagaatg gaagaacaat      60
tataga                                                                 66

<210> SEQ ID NO 79
<211> LENGTH: 66
<212> TYPE: DNA
<213> ORGANISM: Streptococcus thermophilus

<400> SEQUENCE: 79
gttttagagc tgtgttgttt cgaatggttc caaaactatg aattgtcaaa ttaacggttg      60
cgctaa                                                                 66

<210> SEQ ID NO 80
<211> LENGTH: 66
<212> TYPE: DNA
<213> ORGANISM: Streptococcus thermophilus

<400> SEQUENCE: 80
gttttagagc tgtgttgttt cgaatggttc caaaaccgat ggaaatgatg gcttgccagg      60
taagga                                                                 66

<210> SEQ ID NO 81
<211> LENGTH: 66
<212> TYPE: DNA
<213> ORGANISM: Streptococcus thermophilus

<400> SEQUENCE: 81
gttttagagc tgtgttgttt cgaatggttc caaaacaatg ggaaagtagc tatatatgat      60
ccagag                                                                 66

<210> SEQ ID NO 82
<211> LENGTH: 66
<212> TYPE: DNA
<213> ORGANISM: Streptococcus thermophilus

<400> SEQUENCE: 82
gttttagagc tgtgttgttt cgaatggttc caaaacgaag gcacaagaaa gtcaaatgcg      60
tagcgc                                                                 66

<210> SEQ ID NO 83
<211> LENGTH: 66
<212> TYPE: DNA
<213> ORGANISM: Streptococcus thermophilus

<400> SEQUENCE: 83
gttttagagc tgtgttgttt cgaatggttc caaaacaatt ttaacagata tagtgtaatc      60
ggtatt                                                                 66

<210> SEQ ID NO 84
<211> LENGTH: 66
<212> TYPE: DNA
<213> ORGANISM: Streptococcus thermophilus

<400> SEQUENCE: 84
gttttagagc tgtgttgttt cgaatggttc caaaacctat tactatactt ccgaagagat      60
```

```
tgcaga                                                              66

<210> SEQ ID NO 85
<211> LENGTH: 66
<212> TYPE: DNA
<213> ORGANISM: Streptococcus thermophilus

<400> SEQUENCE: 85
gttttagagc tgtgttgttt cgaatggttc caaaactatc ccagagaatg gaagaacaat    60
tataga                                                              66

<210> SEQ ID NO 86
<211> LENGTH: 66
<212> TYPE: DNA
<213> ORGANISM: Streptococcus thermophilus

<400> SEQUENCE: 86
gttttagagc tgtgttgttt cgaatggttc caaaactatg aattgtcaaa ttaacggttg    60
cgctaa                                                              66

<210> SEQ ID NO 87
<211> LENGTH: 63
<212> TYPE: DNA
<213> ORGANISM: Streptococcus thermophilus
<220> FEATURE:
<221> NAME/KEY: misc_feature
<222> LOCATION: (37)..(63)
<223> OTHER INFORMATION: n is a, c, g, or t

<400> SEQUENCE: 87
gttttagagc tgtgttgttt cgaatggttc caaaacnnnn nnnnnnnnn nnnnnnnnn      60 nnn                                                                 63

<210> SEQ ID NO 88
<211> LENGTH: 64
<212> TYPE: DNA
<213> ORGANISM: Streptococcus thermophilus
<220> FEATURE:
<221> NAME/KEY: misc_feature
<222> LOCATION: (37)..(64)
<223> OTHER INFORMATION: n is a, c, g, or t

<400> SEQUENCE: 88
gttttagagc tgtgttgttt cgaatggttc caaaacnnnn nnnnnnnnn nnnnnnnnn      60 nnnn                                                                64

<210> SEQ ID NO 89
<211> LENGTH: 65
<212> TYPE: DNA
<213> ORGANISM: Streptococcus thermophilus
<220> FEATURE:
<221> NAME/KEY: misc_feature
<222> LOCATION: (37)..(65)
<223> OTHER INFORMATION: n is a, c, g, or t

<400> SEQUENCE: 89
gttttagagc tgtgttgttt cgaatggttc caaaacnnnn nnnnnnnnn nnnnnnnnn      60 nnnnn                                                               65

<210> SEQ ID NO 90
<211> LENGTH: 66
<212> TYPE: DNA
```

```
<213> ORGANISM: Streptococcus thermophilus
<220> FEATURE:
<221> NAME/KEY: misc_feature
<222> LOCATION: (37)..(66)
<223> OTHER INFORMATION: n is a, c, g, or t

<400> SEQUENCE: 90
gttttagagc tgtgttgttt cgaatggttc caaaacnnnn nnnnnnnnnn nnnnnnnnnn      60 nnnnnn                                                                 66

<210> SEQ ID NO 91
<211> LENGTH: 67
<212> TYPE: DNA
<213> ORGANISM: Streptococcus thermophilus
<220> FEATURE:
<221> NAME/KEY: misc_feature
<222> LOCATION: (37)..(67)
<223> OTHER INFORMATION: n is a, c, g, or t

<400> SEQUENCE: 91
gttttagagc tgtgttgttt cgaatggttc caaaacnnnn nnnnnnnnnn nnnnnnnnnn      60 nnnnnnn                                                                67

<210> SEQ ID NO 92
<211> LENGTH: 68
<212> TYPE: DNA
<213> ORGANISM: Streptococcus thermophilus
<220> FEATURE:
<221> NAME/KEY: misc_feature
<222> LOCATION: (37)..(68)
<223> OTHER INFORMATION: n is a, c, g, or t

<400> SEQUENCE: 92
gttttagagc tgtgttgttt cgaatggttc caaaacnnnn nnnnnnnnnn nnnnnnnnnn      60 nnnnnnnn                                                               68

<210> SEQ ID NO 93
<211> LENGTH: 69
<212> TYPE: DNA
<213> ORGANISM: Streptococcus thermophilus
<220> FEATURE:
<221> NAME/KEY: misc_feature
<222> LOCATION: (37)..(69)
<223> OTHER INFORMATION: n is a, c, g, or t

<400> SEQUENCE: 93
gttttagagc tgtgttgttt cgaatggttc caaaacnnnn nnnnnnnnnn nnnnnnnnnn      60 nnnnnnnnn                                                              69

<210> SEQ ID NO 94
<211> LENGTH: 66
<212> TYPE: DNA
<213> ORGANISM: Streptococcus thermophilus

<400> SEQUENCE: 94
gttttagagc tgtgttgttt cgaatggttc caaaacagac ccacaaatgg cacttaaaga      60
tgcaat                                                                 66

<210> SEQ ID NO 95
<211> LENGTH: 66
<212> TYPE: DNA
<213> ORGANISM: Streptococcus thermophilus

<400> SEQUENCE: 95
```

```
gttttagagc tgtgttgttt cgaatggttc caaaactatt gtagacactg ggaacggtgg        60
ttatta                                                                   66
```

<210> SEQ ID NO 96
<211> LENGTH: 66
<212> TYPE: DNA
<213> ORGANISM: Streptococcus thermophilus

<400> SEQUENCE: 96

```
gttttagagc tgtgttgttt cgaatggttc caaaactaga ggtaatgacg gcttaccggg        60
taaaga                                                                   66
```

<210> SEQ ID NO 97
<211> LENGTH: 66
<212> TYPE: DNA
<213> ORGANISM: Streptococcus thermophilus

<400> SEQUENCE: 97

```
gttttagagc tgtgttgttt cgaatggttc caaaacttag ccttaagcgg cattaagaag        60
cttggt                                                                   66
```

<210> SEQ ID NO 98
<211> LENGTH: 66
<212> TYPE: DNA
<213> ORGANISM: Streptococcus thermophilus

<400> SEQUENCE: 98

```
gttttagagc tgtgttgttt cgaatggttc caaaaccaaa taatattaat aaccctaacc        60
gtacca                                                                   66
```

<210> SEQ ID NO 99
<211> LENGTH: 66
<212> TYPE: DNA
<213> ORGANISM: Streptococcus thermophilus

<400> SEQUENCE: 99

```
gttttagagc tgtgttgttt cgaatggttc caaaacttgt ggcacaaaca aaatgaatta        60
aagatt                                                                   66
```

<210> SEQ ID NO 100
<211> LENGTH: 66
<212> TYPE: DNA
<213> ORGANISM: Streptococcus thermophilus

<400> SEQUENCE: 100

```
gttttagagc tgtgttgttt cgaatggttc caaaactgta gacgacacaa tgaaacgtgt        60
gattta                                                                   66
```

<210> SEQ ID NO 101
<211> LENGTH: 66
<212> TYPE: DNA
<213> ORGANISM: Streptococcus thermophilus

<400> SEQUENCE: 101

```
gttttagagc tgtgttgttt cgaatggttc caaaactcca gttctaacga cactaaaact        60
aagcga                                                                   66
```

<210> SEQ ID NO 102

```
<211> LENGTH: 67
<212> TYPE: DNA
<213> ORGANISM: Streptococcus thermophilus

<400> SEQUENCE: 102
gttttagagc tgtgttgttt cgaatggttc caaaacaaat tacctctagc gcttctttat    60
aatagct                                                              67

<210> SEQ ID NO 103
<211> LENGTH: 66
<212> TYPE: DNA
<213> ORGANISM: Streptococcus thermophilus

<400> SEQUENCE: 103
gttttagagc tgtgttgttt cgaatggttc caaaaccaat ccagaggtta atcaagcagt    60
attcaa                                                               66
```

STREPTOCOCCUS THERMOPHILUS STRAINS

CROSS-REFERENCE TO RELATED PATENT APPLICATIONS

This patent claims priority under 35 USC § 371 as a national phase of Int'l Patent Appl. PCT/EP2014/065286 (filed Jul. 16, 2014; and published Jan. 22, 2015 as Int'l Publ. No. WO2015/007791), which, in turn, claims priority to European Patent Appl. No. 13176911.9 (filed Jul. 17, 2013). The entire texts of the above-referenced patent applications are incorporated by reference into this patent.

FIELD OF THE INVENTION

The present invention relates to *Streptococcus thermophilus* strains, usable as starter cultures, able to provide both satisfactory rheological and organoleptic properties, and satisfactory shelf life to the media into which they are incorporated. In particular, these strains are also bacteriophage-resistant, thereby minimizing bacteriophage infection. The invention also provides a composition comprising one of these *Streptococcus thermophilus* strains, and feed or food products obtained with these strains.

BACKGROUND OF THE INVENTION

The food industry uses bacteria in order to improve the taste and the texture of food or feed products. In the case of the dairy industry, lactic acid bacteria are commonly used in order to, for example, bring about the acidification of milk (by fermentation) and to texturize the product into which they are incorporated. Among the lactic acid bacteria commonly used in the food industry, examples include the genera *Streptococcus, Lactococcus, Lactobacillus, Leuconostoc, Pediococcus* and *Bifidobacterium*.

The lactic acid bacteria of the species *Streptococcus thermophilus* (*S. thermophilus*) are used extensively, alone or in combination with other bacteria, for the production of food or feed products, in particular fermented products. They are used in particular in the formulation of the starter cultures used for the production of fermented milks, for example yoghurts. *S. thermophilus* is widely used for the manufacture of yoghurt and cheeses, such as Emmental, Gouda, Cheddar and Italian cheeses. These products have a high market value, making *S. thermophilus* a species that has major economic importance.

There is a continuing need in the art to provide bacterial strains, in particular *S. thermophilus* strains, which are able to provide not only good or improved rheological or organoleptic properties, such as texture and flavor, but also a satisfactory shelf life to food or feed products.

SUMMARY OF THE INVENTION

The invention provides a *Streptococcus thermophilus* strain, wherein the milk acidification kinetics of said strain is characterized by an average speed of acidification between pH 6.00 and pH 5.30 which is at least $70\times10^{-4}$ UpH/min or equals $70\times10^{-4}$ UpH/min, and an average speed of acidification between pH 5.30 and pH 5.00 which is less than $22\times10^{-4}$ UpH/min or equals $22\times10^{-4}$ UpH/min, and/or a ratio of (1) average speed of acidification between pH 5.30 and pH 5.00 to (2) average speed of acidification between pH 6.00 and pH 5.30, which is less than or equals 25%. In a particular embodiment, this strain is the DSM 27029 strain, the DSM 27030 strain, or the DSM 27031 strain, all deposited on Mar. 21, 2013 at the Leibniz-Institut DSMZ.

The invention also provides a composition comprising or consisting of a culture of the *Streptococcus thermophilus* strain of the invention, and optionally further comprising at least one other microorganism, in particular at least one other culture(s) of lactic acid bacteria or propionic bacteria.

The invention also relates to the use of a culture of *S. thermophilus* strain or a composition of the invention for preparing a product, in particular food or feed product, in particular fermented product, in particular fermented food or fermented feed product.

The invention is also directed to a method for preparing a product, in particular a fermented product, wherein said method comprises putting into contact a substrate, in particular milk substrate, with or in the presence of the *S. thermophilus* strain or a composition of the invention, optionally fermenting said substrate, and obtaining said product.

The invention also provides a product, in particular a dairy product, in particular a fermented product, comprising a culture of the *S. thermophilus* strain or the composition of the invention.

DESCRIPTION OF THE INVENTION

Figure 1:
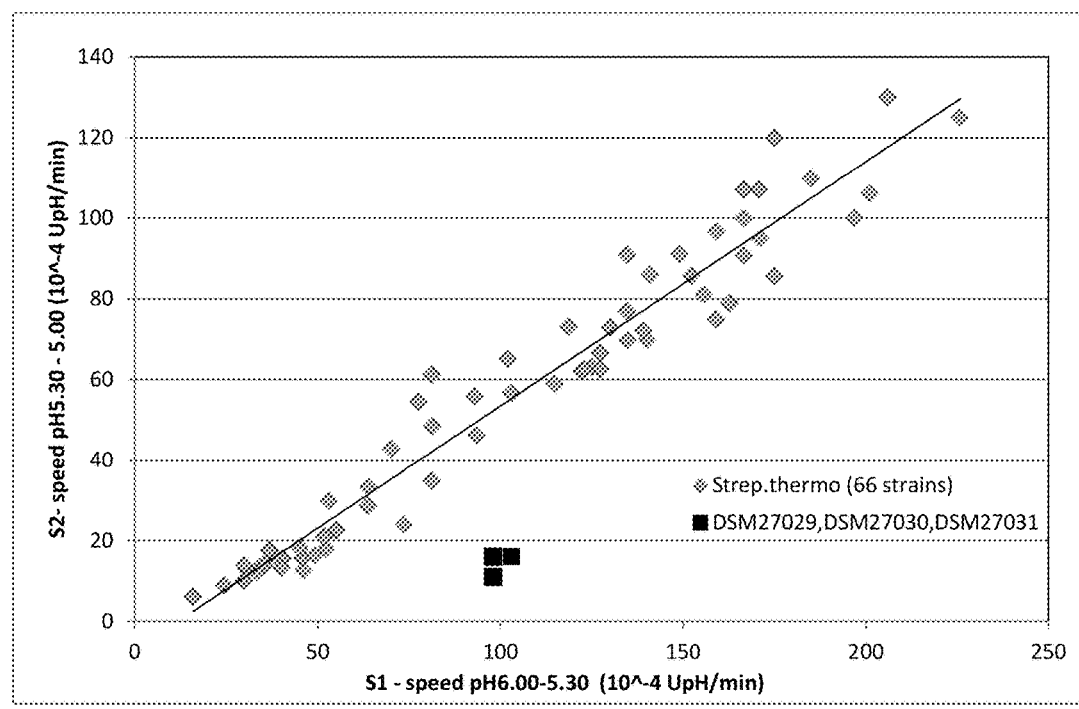
FIG. 1: average speed of acidification between pH 5.30 and pH 5.00 (S2) as a function of the average speed of acidification between pH 6.00 and pH 5.30 (S1), for 69 *S. thermophilus* strains. Examples of strains of the invention are represented by black squares, as compared to other *S. thermophilus* strains (grey diamonds).

The inventors have identified *Streptococcus thermophilus* strains having surprising and atypical milk acidification kinetics. The inventors have shown that these strains may be used for the production or fermentation of feed or food products. In particular, these strains give products with satisfactory rheological and/or organoleptic properties, as well as product with a satisfactory shelf life, at least similar to the products obtained using already existing *Streptococcus thermophilus* strains. Interestingly, the study of more than 60 known *Streptococcus thermophilus* strains, disclosed in previous patent applications or in the literature, has enabled to identify *S. thermophilus* strains with atypical milk acidification kinetics.

The invention provides a *Streptococcus thermophilus* strain, wherein the milk acidification kinetics of said strain is characterized by:
- an average speed of acidification between pH 6.00 and pH 5.30 which is at least $70\times10^{-4}$ UpH/min or equals $70\times10^{-4}$ UpH/min, and
- an average speed of acidification between pH 5.30 and pH 5.00 which is less than $22\times10^{-4}$ UpH/min or equals $22\times10^{-4}$ UpH/min.

The average speed of acidification between pH 6.00 and pH 5.30 is referred to in the present application as S1. The average speed of acidification between pH 5.30 and pH 5.00 is referred to in the present application as S2. The average speed of acidification between pH 6.00 and pH 5.30 and the average speed of acidification between pH 5.30 and pH 5.00 are determined in milk substrate, in particular in cow milk (milk acidification kinetics), such as "Le Petit Vendéen". Both average speeds of acidification S1 and S2 are determined by any conventional means. In particular, S1 and S2 are calculated using a Cinac system (CINAC, an automated system for control of lactic starters; Corrieu G, Picque D, Perret B, Quemener P; Process Magazine; 1992: 1068; p. 24-27). An automated system for measuring the rate of acidification is well known to the person of ordinary skill in the art. Reference can be found, for example, in patent FR2629612. S1 and S2 are calculated from the same sample, in particular from the same milk acidification curve. An example of data obtained using the CINAC system and enabling the calculations of the average speeds of acidification S1 and S2, is disclosed in example 1.

In a particular embodiment, S1 and S2 are calculated as described in or using the assay presented as Assay I (defined in details in example 1 below). It is noteworthy that S1 and S2 are calculated using only a single *S. thermophilus* strain.

In a particular embodiment, the invention provides a *Streptococcus thermophilus* strain, wherein the milk acidification kinetics of said strain is characterized by:
  an average speed of acidification between pH 6.00 and pH 5.30 which is between $70 \times 10^{-4}$ and $250 \times 10^{-4}$ UpH/min, between $70 \times 10^{-4}$ and $200 \times 10^{-4}$ UpH/min, between $70 \times 10^{-4}$ or between $180 \times 10^{-4}$ UpH/min, or $70 \times 10^{-4}$ and $140 \times 10^{-4}$ UpH/min; and
  an average speed of acidification between pH 5.30 and pH 5.00 which is between $1 \times 10^{-4}$ and $20 \times 10^{-4}$ UpH/min, between $2 \times 10^{-4}$ and $22 \times 10^{-4}$ UpH/min, or between $2 \times 10^{-4}$ and $20 \times 10^{-4}$ UpH/min.

In a particular embodiment, the invention is directed to a *Streptococcus thermophilus* strain, wherein the milk acidification kinetics of said strain is characterized by:
  an average speed of acidification between pH 6.00 and pH 5.30 which is between $70 \times 10^{-4}$ and $250 \times 10^{-4}$, $70 \times 10^{-4}$ and $200 \times 10^{-4}$, $70 \times 10^{-4}$ and $180 \times 10^{-4}$, or $70 \times 10^{-4}$ and $140 \times 10^{-4}$ UpH/min, calculated as described in Assay I; and
  an average speed of acidification between pH 5.30 and pH 5.00 which is between $1 \times 10^{-4}$ and $20 \times 10^{-4}$, $2 \times 10^{-4}$ and $22 \times 10^{-4}$, or $2 \times 10^{-4}$ and $20 \times 10^{-4}$ UpH/min, calculated as described in Assay I.

In a more particular embodiment, the average speed of acidification between pH 6.00 and pH 5.30 (S1), preferably calculated as described in Assay I, is between $80 \times 10^{-4}$ and $120 \times 10^{-4}$, between $90 \times 10^{-4}$ and $110 \times 10^{-4}$, or between $95 \times 10^{-4}$ and $105 \times 10^{-4}$ UpH/min.

In a more particular embodiment, the average speed of acidification between pH 5.30 and pH 5.00 (S2), preferably calculated as described in Assay I, is between $5 \times 10^{-4}$ and $20 \times 10^{-4}$ UpH/min, or between $10 \times 10^{-4}$ and $18 \times 10^{-4}$ UpH/min.

In a particular embodiment, the invention is directed to a *Streptococcus thermophilus* strain, wherein the milk acidification kinetics of said strain is characterized by:
  an average speed of acidification between pH 6.00 and pH 5.30 which is between $70 \times 10^{-4}$ and $250 \times 10^{-4}$, between $70 \times 10^{-4}$ and $200 \times 10^{-4}$, between $70 \times 10^{-4}$ and $180 \times 10^{-4}$, between $70 \times 10^{-4}$ and $140 \times 10^{-4}$, between $80 \times 10^{-4}$ and $120 \times 10^{-4}$, between $90 \times 10^{-4}$ and $110 \times 10^{-4}$, or between $95 \times 10^{-4}$ and $105 \times 10^{-4}$ UpH/min, preferably calculated as described in Assay I, and
  an average speed of acidification between pH 5.30 and pH 5.00 which is between $1 \times 10^{-4}$ and $20 \times 10^{-4}$, between $2 \times 10^{-4}$ and $22 \times 10^{-4}$, between $2 \times 10^{-4}$ and $20 \times 10^{-4}$, between $5 \times 10^{-4}$ and $20 \times 10^{-4}$ or between $10 \times 10^{-4}$ and $18 \times 10^{-4}$ UpH/min, preferably calculated as described in Assay I.

The invention also provides a *Streptococcus thermophilus* strain, wherein the milk acidification kinetics of said strain is characterized by a ratio of (1) average speed of acidification between pH 5.30 and pH 5.00, preferably calculated as described in Assay I, to (2) average speed of acidification between pH 6.00 and pH 5.30, preferably calculated as described in Assay I, which is less than or equals 25%, or is less than or equals 20%, or is less than or equals 18%. Average speed of acidification between pH 6.00 and pH 5.30 and average speed of acidification between pH 5.30 and pH 5.00 are defined and determined according to the embodiments as described above. The ratio (in %) is calculated as follows [ratio of S2 to S1 or S2/S1 ratio]:

$$\frac{\text{average speed of acidification between pH 5.30 and pH 5.00 (S2)}}{\text{average speed of acidification between pH 6.00 and pH 5.30 (S1)}} \times 100$$

As mentioned above, S1 and S2 are calculated from the same sample, in particular from the same acidification curve when using the CINAC system.

In a particular embodiment, the S2/S1 ratio is between 1 and 25%, between 2 and 25%, between 5 and 18%, between 8 to 18% or between 10 and 18%.

In a particular embodiment, the invention provides a *Streptococcus thermophilus* strain wherein the milk acidification kinetics of said strain is characterized by:
  an average speed of acidification between pH 6.00 and pH 5.30 which is at least $70 \times 10^{-4}$ UpH/min or equals $70 \times 10^{-4}$ UpH/min, and
  an average speed of acidification between pH 5.30 and pH 5.00 which is less than $22 \times 10^{-4}$ UpH/min or equals $22 \times 10^{-4}$ UpH/min, and
  a ratio of (1) average speed of acidification between pH 5.30 and pH 5.00 to (2) average speed of acidification between pH 6.00 and pH 5.30, which is less than or equals 25% or less than or equals 20%, or less than or equals 18%, wherein preferably the average speed of acidification between pH 6.00 and pH 5.30 and the average speed of acidification between pH 5.30 and pH 5.00 are calculated as described in Assay I.

Average speed of acidification between pH 6.00 and pH 5.30 and average speed of acidification between pH 5.30 and pH 5.00 are defined and determined according to the embodiments as described above.

In a particular embodiment, the invention provides a *Streptococcus thermophilus* strain wherein the milk acidification kinetics of said strain is characterized by:
  an average speed of acidification between pH 6.00 and pH 5.30 which is between $70 \times 10^{-4}$ and $250 \times 10^{-4}$, between $70 \times 10^{-4}$ and $200 \times 10^{-4}$, between $70 \times 10^{-4}$ and $180 \times 10^{-4}$, between $70 \times 10^{-4}$ and $140 \times 10^{-4}$, between $80 \times 10^{-4}$ and $120 \times 10^{-4}$, between $90 \times 10^{-4}$ and $110 \times 10^{-4}$, or between $95 \times 10^{-4}$ and $105 \times 10^{-4}$ UpH/min, and
  an average speed of acidification between pH 5.30 and pH 5.00 which is between $1 \times 10^{-4}$ and $20 \times 10^{-4}$, between $2 \times 10^{-4}$ and $22 \times 10^{-4}$, between $2 \times 10^{-4}$ and $20 \times 10^{-4}$, between $5 \times 10^{-4}$ and $20 \times 10^{-4}$ or between $10 \times 10^{-4}$ and $18 \times 10^{-4}$ UpH/min, and a ratio of (1) average speed of acidification between pH 5.30 and pH 5.00 to (2) average speed of acidification between pH 6.00 and pH 5.30, which is between 1 and 25%, between 2 and 25%, between 5 and 18%, between 8 to 18% or between 10 and 18%, wherein preferably the average speed of acidification between pH 6.00 and pH 5.30 and the average speed of acidification between pH 5.30 and pH 5.00 are calculated as described in Assay I.

Average speed of acidification between pH 6.00 and pH 5.30 and average speed of acidification between pH 5.30 and pH 5.00 are defined and determined according to the embodiments as described above.

The invention relates to any *Streptococcus thermophilus* strain defined by the combination of any S2/S1 ratio range or maximum as disclosed herein, with any S2 range or maximum as herein disclosed, and with any S1 range or minimum as herein disclosed.

As a particular embodiment, the invention provides a *Streptococcus thermophilus* strain wherein the milk acidification kinetics of said strain is characterized by:

an average speed of acidification between pH 6.00 and pH 5.30 which is between $90 \times 10^{-4}$ and $110 \times 10^{-4}$ UpH/min, or between $95 \times 10^{-4}$ and $105 \times 10^{-4}$ UpH/min; and an average speed of acidification between pH 5.30 and pH 5.00 which is between $5 \times 10^{-4}$ and $20 \times 10^{-4}$ UpH/min or between $10 \times 10^{-4}$ and $18 \times 10^{-4}$ UpH/min; and a ratio of (1) average speed of acidification between pH 5.30 and pH 5.00 to (2) average speed of acidification between pH 6.00 and pH 5.30, which is between 8 to 18% or between 10 and 18%, wherein preferably the average speed of acidification between pH 6.00 and pH 5.30 and the average speed of acidification between pH 5.30 and pH 5.00 are calculated as described in Assay I.

The particular features described herein regarding the speed of acidification between pH 5.30 and pH 5.00 (S2), regarding the average speed of acidification between pH 6.00 and pH 5.30 (S1), regarding the S2/S1 ratio and/or regarding the methods of calculation of S1 and S2, in particular the CINAC system, apply to all the embodiments of the *S. thermophilus* strain of the invention as defined herein in the application.

Whereas all the known *S. thermophilus* strains present a tight link between the average speed of acidification between pH 5.30 and pH 5.00 (S2), and the average speed of acidification between pH 6.00 and pH 5.30 (S1) [i.e., the highest the S1 value, the highest the S2 value], the invention provides herein for the first time *Streptococcus thermophilus* strains for which the average speed of acidification between pH 5.30 and pH 5.00 (S2) is uncoupled from the average speed of acidification between pH 6.00 and pH 5.30 (S1).

The invention also provides a *Streptococcus thermophilus* strain of the invention which is further characterized, in addition to a) its average speed of acidification between pH 6.00 and pH 5.30 (S2) as defined herein and its average speed of acidification between pH 5.30 and pH 5.00 (S1) as defined herein, and/or b) its S2/S1 ratio as defined herein, by the presence in its genome of at least one element selected from the group consisting of a CRISPR4 locus, a CRISPR1 locus, and a CRISPR3 locus, each element being defined hereinafter.

The common structural characteristics of a CRISPR-Cas system are described in Jansen et al. (2002, Janssen et al. (2002) OMICSJ. Integ. Biol. 6:23-33) as (i) the presence of multiple short direct repeats (CRISPR repeats), which are typically short partially palindromic sequences of 24-40 bp containing inner and terminal inverted repeats of up to 11 bp and show no or very little sequence variation within a given locus; (ii) the presence of non-repetitive spacer sequences (CRISPR spacers) of similar size between the repeats; (iii) the presence of a common leader sequence of a dozen to a few hundred base pairs in most species harbouring multiple CRISPR loci; and (iv) the presence of one or more cas (CRISPR-associated) genes.

Within the present invention, the expression "CRISPR locus" refers to a DNA segment which consists of at least one [repeat-spacer] unit and a terminal repeat, starting with the first nucleotide of the first CRISPR repeat and ending with the last nucleotide of the terminal (last) CRISPR repeat. Thus, a CRISPR locus consists of at least one [repeat-spacer] unit, in particular several [repeat-spacer] units (said several [repeat-spacer] units having an identical or at least similar CRISPR repeat sequence for all the units), followed by a last terminal repeat (the sequence of which is identical or similar, notably in its 5' part, to the CRISPR repeat sequence of the units). In the context of the present invention, the CRISPR locus (either CRISPR1, CRISPR3, or CRISPR4 locus) is orientated as follows. The CRISPR leader is a DNA segment, which is generally A/T-rich, located immediately upstream of the first CRISPR repeat of the CRISPR locus. The CRISPR trailer is a DNA segment located immediately downstream of the terminal repeat. Therefore, the CRISPR locus is located between the CRISPR leader and the CRISPR trailer.

In a first embodiment, the invention provides a *Streptococcus thermophilus* strain as defined herein, whose genome comprises a CRISPR4 locus. In a particular embodiment, the invention provides a *Streptococcus thermophilus* strain as defined herein, whose genome comprises a CRISPR4 locus as defined in SEQ ID NO:3 or comprises a CRISPR4 locus comprising part(s) of SEQ ID NO:3. SEQ ID NO:3 contains 12 CRISPR4 [repeat-spacer] units and a terminal repeat. The sequence of these 12 CRISPR4 [repeat-spacer] units of SEQ ID NO:3 are as defined in SEQ ID NO:4 to SEQ ID NO:15, respectively. The sequence of the CRISPR4 terminal repeat is as defined in SEQ ID NO:16. The CRISPR4 leader and CRISPR4 trailer sequences flanking the CRISPR4 locus of a particular embodiment of *Streptococcus thermophilus* strains of the invention are as defined in SEQ ID NO:2 and SEQ ID NO:1, respectively.

In a particular embodiment, the invention provides a *Streptococcus thermophilus* strain as defined herein, whose genome comprises a CRISPR4 locus comprising or consisting of the sequence as defined in SEQ ID NO:3.

In a particular embodiment, the invention provides a *Streptococcus thermophilus* strain as defined herein, whose genome comprises a CRISPR4 locus comprising, from 5' to 3', a part of SEQ ID NO:3 and a terminal repeat as defined in SEQ ID NO:16.

By "part of SEQ ID NO:3", in the context of the CRISPR4 locus, it is meant a fragment of SEQ ID NO:3 which comprises at least or exactly 3 consecutive CRISPR4 [repeat-spacer] units contained in SEQ ID NO:3, in particular at least or exactly 3, 4, 5, 6, 7, 8, 9, 10 or 11, consecutive [repeat-spacer] units contained in SEQ ID NO:3. By "consecutive", it is meant that the CRISPR4 [repeat-spacer] units in said part of SEQ ID NO:3 are found and linked in the same order as they appear in SEQ ID NO:3 (e.g., SEQ ID NO:4-SEQ ID NO:5-SEQ ID NO:6, or SEQ ID NO:10-SEQ ID NO:11-SEQ ID NO:12). In a particular embodiment, a part of SEQ ID NO:3 is a fragment of SEQ ID NO:3 which comprises at least or exactly 3 consecutive CRISPR4 [repeat-spacer] units selected from the group consisting of SEQ ID NO:4 to SEQ ID NO:15. In a particular embodiment, "part of SEQ ID NO:3" refers to the 3, 4, 5, 6, 7, 8, 9, 10, or 11 consecutive terminal CRISPR4 [repeat-spacer] units contained in SEQ ID NO:3. By "terminal CRISPR4 [repeat-spacer] units contained in SEQ ID NO:3", it is meant the CRISPR4 [repeat-spacer] units which are located the most 3' (i.e. at the trailer end) in the CRISPR4 locus of SEQ ID NO:3, i.e., immediately before the terminal repeat as defined in SEQ ID NO:16. Thus, the two consecutive terminal CRISPR4 [repeat-spacer] units of SEQ ID NO:3 mean SEQ ID NO:14-SEQ ID NO:15, the 3 consecutive terminal CRISPR4 [repeat-spacer] units of SEQ ID NO:3 mean SEQ ID NO:13-SEQ ID NO:14-SEQ ID NO:15, etc.

In a second embodiment, as such or in combination with the first embodiment, the invention provides a *Streptococcus thermophilus* strain as defined herein, whose genome comprises a CRISPR1 locus.

In a particular embodiment, the invention provides a *Streptococcus thermophilus* strain as defined herein, whose genome comprises a CRISPR1 locus comprising or consisting of the sequence as defined in SEQ ID NO:19 or a CRISPR1 locus comprising part(s) of SEQ ID NO:19.

SEQ ID NO:19 contains 32 CRISPR1 [repeat-spacer] units and 1 terminal repeat, the sequence of which is similar but different from the repeat of the 32 CRISPR1 [repeat-spacer] units. The sequence of these 32 CRISPR1 [repeat-spacer] units of SEQ ID NO:19 are as defined in SEQ ID NO:22 to SEQ ID NO:53, respectively. The sequence of the repeat of all the CRISPR1 [repeat-spacer] unit(s), within the CRISPR1 locus defined herein, is as defined in SEQ ID NO:20 (R1). The sequence of the terminal repeat is as defined in SEQ ID NO:21 (R' 1). It is noteworthy that any In a particular embodiment, the CRISPR1 locus as defined in SEQ ID NO:19 or the CRISPR1 locus comprising part(s) of SEQ ID NO:19 as defined herein, is flanked by the CRISPR1 leader and the CRISPR1 trailer sequences, as defined in SEQ ID NO:17 and SEQ ID NO:18, respectively.

Following phage challenge, one or more additional CRISPR1 [repeat-spacer] unit(s) may be added within the CRISPR locus, in particular at the 5' part (i.e. the leader end) of the CRISPR1 locus as defined herein, i.e., immediately after the last nucleotide of the CRISPR1 leader sequence. This (these) additional CRISPR1 [repeat-spacer] unit(s) has (have) a sequence defined, from 5' to 3', as R1-X1, wherein R1 is as defined in SEQ ID NO:20, and X1 is any sequence with a length from 27 to 33 by, in particular from 28 to 32 bp, in particular from 29 to 31 bp, and in particular exactly 30 bp. In particular, the sequence of any of these additional CRISPR1 [repeat-spacer] unit(s) is chosen in the group consisting of SEQ ID NO:54, SEQ ID NO:55, SEQ ID NO:56, SEQ ID NO:57, SEQ ID NO:58, SEQ ID NO:59, or SEQ ID NO:60. Non-limiting examples of additional CRISPR1 [repeat-spacer] unit(s), which can be used according to the invention, are as defined in SEQ ID NO:61 to SEQ ID NO:70.

In a particular embodiment, the invention provides a *Streptococcus thermophilus* strain as defined herein, whose genome comprises a CRISPR1 locus comprising or consisting of the sequence as defined in SEQ ID NO:19. In a particular embodiment, the CRISPR1 locus consists of, from 5' to 3', at least one additional CRISPR1 [repeat-spacer] unit of sequence R1-X1, in particular at least 1, 2, 3, 4, 5, 6, 7, 8, 9, 10, 15, 20, 30 or more additional CRISPR1 [repeat-spacer] unit(s) of sequence R1-X1, and SEQ ID NO:19.

In a particular embodiment, the invention provides a *Streptococcus thermophilus* strain as defined herein, whose genome comprises a CRISPR1 locus comprising, from 5' to 3', a part of SEQ ID NO:19 and a terminal repeat as defined in SEQ ID NO:21.

By "part of SEQ ID NO:19", in the context of the CRISPR1 locus, it is meant a fragment of SEQ ID NO:19 which comprises at least or exactly 3 consecutive CRISPR1 [repeat-spacer] units contained in SEQ ID NO:19, in particular at least or exactly 3, 4, 5, 6, 7, 8, 9, 10, 11, 12, 13, 14, 15, 16, 17, 18, 19, 20, 21, 22, 23, 24, 25, 26, 27, 28, 29, 30, or 31 consecutive [repeat-spacer] units contained in SEQ ID NO:19. By "consecutive", it is meant that the CRISPR1 [repeat-spacer] units in said part of SEQ ID NO:19 are found and linked in the same order as they appear in SEQ ID NO:19 (e.g., SEQ ID NO:23-SEQ ID NO:24-SEQ ID NO:25, or SEQ ID NO:42-SEQ ID NO:43-SEQ ID NO:44). In a particular embodiment, a part of SEQ ID NO:19 is a fragment of SEQ ID NO:19 which comprises at least or exactly 3 consecutive CRISPR1 [repeat-spacer] units selected from the group consisting of SEQ ID NO:22 to SEQ ID NO. 53. In a particular embodiment, "part of SEQ ID NO:19" refers to the 3, 4, 5, 6, 7, 8, 9, 10, 11, 12, 13, 14, 15, 16, 17, 18, 19, 20, 21, 22, 23, 24, 25, 26, 27, 28, 29, 30, or 31 consecutive terminal CRISPR1 [repeat-spacer] units contained in SEQ ID NO:19. By "terminal CRISPR1 [repeat-spacer] units contained in SEQ ID NO:19", it is meant the CRISPR1 [repeat-spacer] units which are located the most 3' (i.e. at the trailer end) in the CRISPR1 locus of SEQ ID NO:19, i.e., immediately before the R1' terminal repeat as defined in SEQ ID NO:21. Thus, the two consecutive terminal CRISPR1 [repeat-spacer] units of SEQ ID NO:19 mean SEQ ID NO:52-SEQ ID NO:53, the 3 consecutive terminal CRISPR1 [repeat-spacer] units of SEQ ID NO:19 mean SEQ ID NO:51-SEQ ID NO:52-SEQ ID NO:53, etc.

In a particular embodiment, the CRISPR1 locus consists of, from 5' to 3', an integer number of [repeat-spacer] units, including at least 3 consecutive CRISPR1 [repeat-spacer] units contained in SEQ ID NO:19 (part of SEQ ID NO:19 as defined herein), and the terminal repeat of SEQ ID NO:21. In a particular embodiment, the CRISPR1 locus consists of, from 5' to 3', an integer number of [repeat-spacer] units, including at least 3 consecutive CRISPR1 [repeat-spacer] units selected from the group consisting of SEQ ID NO:22 to SEQ ID NO:53, and the terminal repeat of SEQ ID NO:21. In a particular embodiment, the CRISPR1 locus consists of, from 5' to 3', at least one additional CRISPR1 [repeat-spacer] unit of sequence R1-X1, in particular at least 1, 2, 3, 4, 5, 6, 7, 8, 9, 10, 15, 20, 30 or more additional CRISPR1 [repeat-spacer] unit(s) of sequence R1-X1, at least 3 consecutive CRISPR1 [repeat-spacer] units contained in SEQ ID NO:19 (part of SEQ ID NO:19), and the terminal repeat of SEQ ID NO:21.

In a particular embodiment, the CRISPR1 locus consists of, from 5' to 3', at least one additional CRISPR1 [repeat-spacer] unit of sequence R1-X1, in particular at least 1, 2, 3, 4, 5, 6, 7, 8, 9, 10, 15, 20, 30 or more additional CRISPR1 [repeat-spacer] unit(s) of sequence R1-X1, a part of SEQ ID NO:19 as defined above, and the terminal repeat of SEQ ID NO:21. In a particular embodiment, the CRISPR1 locus consists of, from 5' to 3', at least one additional CRISPR1 [repeat-spacer] unit of sequence R1-X1, in particular at least 1, 2, 3, 4, 5, 6, 7, 8, 9, 10, 15, 20, 30 or more additional CRISPR1 [repeat-spacer] unit(s) of sequence R1-X1, from 1 to 31 consecutive terminal CRISPR1 [repeat-spacer] units contained in SEQ ID NO:19, and the terminal repeat of SEQ ID NO:21.

In a third embodiment, as such or in combination with the first embodiment, the second embodiment, or the first and second embodiments, the invention provides a *Streptococcus thermophilus* strain as defined herein, whose genome comprises a CRISPR3 locus.

In a particular embodiment, the invention provides a *Streptococcus thermophilus* strain as defined herein, whose genome comprises a CRISPR3 locus comprising or consisting of the sequence as defined in SEQ ID NO:73 or a CRISPR3 locus comprising part(s) of SEQ ID NO:73.

SEQ ID NO:73 contains 12 CRISPR3 [repeat-spacer] units and 1 terminal repeat, the sequence of which is the same as the repeat of the 12 CRISPR3 [repeat-spacer] units. The sequence of these 12 CRISPR3 [repeat-spacer] units of SEQ ID NO:73 are as defined in SEQ ID NO:75 to SEQ ID NO:86, respectively. The sequence of the repeat of all the CRISPR3 [repeat-spacer] unit(s), within the CRISPR3 locus defined herein, is as defined in SEQ ID NO:74 (R3). The sequence of the terminal repeat is identical to R3 and is as defined in SEQ ID NO:74. In a particular embodiment, the CRISPR3 locus as defined in SEQ ID NO:73 or the CRISPR3 locus comprising part(s) of SEQ ID NO:73 as defined herein, is flanked by the CRISPR3 leader and the CRISPR3 trailer sequences as defined in SEQ ID NO:71 and SEQ ID NO:72, respectively.

Following phage challenge, one or more additional CRISPR3 [repeat-spacer] unit(s) may be added within the CRISPR3 locus, in particular at the 5' part (i.e. the leader end) of the CRISPR3 locus as defined herein, i.e., immediately after the last nucleotide of the CRISPR3 leader sequence. This (these) additional CRISPR3 [repeat-spacer] unit(s) has (have) a sequence defined, from 5' to 3', as R3-X3, wherein R3 is as defined in SEQ ID NO:74, and X3 is any sequence, in particular any CRISPR spacer sequence, with a length from 27 to 33 bp, in particular from 28 to 32 bp, in particular from 29 to 31 bp, and in particular exactly 30 bp. In particular, the sequence of any of these additional CRISPR3 [repeat-spacer] unit(s) is chosen in the group consisting of SEQ ID NO:87, SEQ ID NO:88, SEQ ID NO:89, SEQ ID NO:90, SEQ ID NO:91, SEQ ID NO:92, or SEQ ID NO:93. Non-limiting examples of additional CRISPR3 [repeat-spacer] unit(s), which can be used according to the invention, are as defined in SEQ ID NO:94 to SEQ ID NO:103.

In a particular embodiment, the invention provides a *Streptococcus thermophilus* strain as defined herein, whose genome comprises a CRISPR3 locus comprising or consisting of the sequence as defined in SEQ ID NO:73. In a particular embodiment, the CRISPR3 locus consists of, from 5' to 3', at least one additional CRISPR3 [repeat-spacer] unit of sequence R3-X3, in particular at least 1, 2, 3, 4, 5, 6, 7, 8, 9, 10, 15, 20, 30 or more additional CRISPR3 [repeat-spacer] unit(s) of sequence R3-X3, and SEQ ID NO:73.

In a particular embodiment, the invention provides a *Streptococcus thermophilus* strain as defined herein, whose genome comprises a CRISPR3 locus comprising, from 5' to 3', a part of SEQ ID NO:73 and a terminal repeat as defined in SEQ ID NO:74.

By "part of SEQ ID NO: 73" in the context of the CRISPR3 locus, it is meant a fragment of SEQ ID NO:73 which comprises at least or exactly 3 consecutive CRISPR3 [repeat-spacer] units contained in SEQ ID NO:73, in particular at least or exactly 3, 4, 5, 6, 7, 8, 9, 10 or 11 consecutive [repeat-spacer] units contained in SEQ ID NO:73. By "consecutive", it is meant that the CRISPR3 [repeat-spacer] units in said part of SEQ ID NO:73 are found and linked in the same order as they appear in SEQ ID NO:73 (e.g., SEQ ID NO: 76-SEQ ID NO:77-SEQ ID NO:78, or SEQ ID NO: 82-SEQ ID NO:83-SEQ ID NO:84).

In a particular embodiment, a part of SEQ ID NO:73 is a fragment of SEQ ID NO:73 which comprises at least or exactly 3 consecutive CRISPR3 [repeat-spacer] units selected from the group consisting of SEQ ID NO:75 to SEQ ID NO:86. In a particular embodiment, "part of SEQ ID NO: 73" refers to the 3, 4, 5, 6, 7, 8, 9, 10, or 11 consecutive terminal CRISPR3 [repeat-spacer] units contained in SEQ ID NO:73. By "terminal CRISPR3 [repeat-spacer] units contained in SEQ ID NO: 73", it is meant the CRISPR3 [repeat-spacer] units which are located the most 3' (i.e., at the trailer end) in the CRISPR3 locus of SEQ ID NO:73, i.e., immediately before the terminal repeat of SEQ ID NO:74. Thus, the two consecutive terminal CRISPR3 [repeat-spacer] units of SEQ ID NO:73 mean SEQ ID NO:85-SEQ ID NO:86, the 3 consecutive terminal CRISPR3 [repeat-spacer] units of SEQ ID NO:73 mean SEQ ID NO:84-SEQ ID NO:85-SEQ ID NO:86, etc.

In a particular embodiment, the CRISPR3 locus consists of, from 5' to 3', an integer number of [repeat-spacer] units, including at least 3 consecutive CRISPR3 [repeat-spacer] units contained in SEQ ID NO:73 (part of SEQ ID NO:73 as defined herein), and the terminal repeat of SEQ ID NO:74. In a particular embodiment, the CRISPR3 locus consists of, from 5' to 3', an integer number of [repeat-spacer] units, including at least 3 consecutive CRISPR3 [repeat-spacer] units selected from the group consisting of SEQ ID NO:75 to SEQ ID NO:86, and the terminal repeat of SEQ ID NO:74. In a particular embodiment, the CRISPR3 locus consists of, from 5' to 3', at least one additional CRISPR3 [repeat-spacer] unit of sequence R3-X3, in particular at least 1, 2, 3, 4, 5, 6, 7, 8, 9, 10, 15, 20, 30 or more additional CRISPR3 [repeat-spacer] unit(s) of sequence R3-X3, at least 3 consecutive CRISPR3 [repeat-spacer] units contained in SEQ ID NO:73 (part of SEQ ID NO:73), and the terminal repeat of SEQ ID NO:74.

In a particular embodiment, the CRISPR3 locus consists of, from 5' to 3', at least one additional CRISPR3 [repeat-spacer] unit of sequence R3-X3, in particular at least 1, 2, 3, 4, 5, 6, 7, 8, 9, 10, 15, 20, 30 or more additional CRISPR3 [repeat-spacer] unit(s) of sequence R3-X3, a part of SEQ ID NO:73 as defined above, and the terminal repeat of SEQ ID NO:74. In a particular embodiment, the CRISPR3 locus consists of, from 5' to 3', at least one additional CRISPR3 [repeat-spacer] unit of sequence R3-X3, in particular at least 1, 2, 3, 4, 5, 6, 7, 8, 9, 10, 15, 20, 30 or more additional CRISPR3 [repeat-spacer] unit(s) of sequence R3-X3, from 1 to 11 consecutive terminal CRISPR3 [repeat-spacer] units contained in SEQ ID NO:73, and the terminal repeat of SEQ ID NO:74.

In a particular embodiment, the invention provides a *Streptococcus thermophilus* strain wherein the milk acidification kinetics of said strain is characterized by:

a) an average speed of acidification between pH 6.00 and pH 5.30 which is at least $70 \times 10^{-4}$ UpH/min or equals $70 \times 10^{-4}$ UpH/min or is between $70 \times 10^{-4}$ and $250 \times 10^{-4}$, between $70 \times 10^{-4}$ and $200 \times 10^{-4}$, between $70 \times 10^{-4}$ and $180 \times 10^{-4}$, between $70 \times 10^{-4}$ and $140 \times 10^{-4}$, between $80 \times 10^{-4}$ and $120 \times 10^{-4}$, between $90 \times 10^{-4}$ and $110 \times 10^{-4}$, or between $95 \times 10^{-4}$ and $105 \times 10^{-4}$ UpH/min, and an average speed of acidification between pH 5.30 and pH 5.00 which is less than $22 \times 10^{-4}$ UpH/min or equals $22 \times 10^{-4}$ UpH/min or is between $1 \times 10^{-4}$ and $20 \times 10^{-4}$, between $2 \times 10^{-4}$ and $22 \times 10^{-4}$, between $2 \times 10^{-4}$ and $20 \times 10^{-4}$, between $5 \times 10^{-4}$ and $20 \times 10^{-4}$ or between $10 \times 10^{-4}$ and $18 \times 10^{-4}$ UpH/min; and/or b) a ratio (1) average speed of acidification between pH 5.30 and pH 5.00 over (2) average speed of acidification between pH 6.00 and pH 5.30, which is less than or equals 25% or less than or equals 20%, less than or equals 18% or is between 1 and 25%, between 2 and 25%, between 5 and 18%, between 8 to 18% or between 10 and 18%,
wherein preferably the average speed of acidification between pH 6.00 and pH 5.30 and the average speed of acidification between pH 5.30 and pH 5.00 are calculated as described in Assay I, and
whose genome comprises at least one element selected from the group consisting of a CRISPR4 locus, a CRISPR1 locus, and a CRISPR3 locus as defined herein, preferably whose genome comprises one, two, or three elements selected from this group.

In a particular embodiment, the *Streptococcus thermophilus* strain of the invention is the strain deposited under the Budapest Treaty on Mar. 21, 2013 in the name of Danisco Deutschland GmbH at the Leibniz-Institut DSMZ-Deutsche Sammlung von Mikroorganismen and Zellkulturen, GmbH (Inhoffenstr. 7B, D-38124 Braunschweig), under number DSM 27029 [herein the DSM 27029 strain].

In another embodiment, the *Streptococcus thermophilus* strain of the invention is the strain deposited under the Budapest Treaty on Mar. 21, 2013 in the name of Danisco Deutschland GmbH at the Leibniz-Institut DSMZ, under number DSM 27030 [herein the DSM 27030 strain].

In another embodiment, the *Streptococcus thermophilus* strain of the invention is the strain deposited under the Budapest Treaty on Mar. 21, 2013 in the name of Danisco Deutschland GmbH at the Leibniz-Institut DSMZ, under number DSM 27031 [herein the DSM 27031 strain].

We hereby confirm that the depositor, Danisco Deutschland GmbH (of Busch-Johannsen-Strasse 1, D-25899 Niebüll, Germany) has authorised the Applicant (DuPont Nutrition Biosciences ApS, Langebrogade 1, DK-1411 Copenhagen K, Denmark) to refer to the deposited biological materials in this application and has given his unreserved and irrevocable consent to the deposited materials being made available to the public.

In respect to those designations in which a European Patent is sought, a sample of the deposited microorganism will be made available until the publication of the mention of the grant of the European patent or until the date on which application has been refused or withdrawn or is deemed to be withdrawn, only by the issue of such a sample to an expert nominated by the person requesting the sample, and approved either i) by the Applicant and/or ii) by the European Patent Office, whichever applies (Rule 32 EPC).

In a particular embodiment, the *Streptococcus thermophilus* strain of the invention is a mutant strain of the DSM 27029 strain, of the DSM 27030 strain, or of the DSM 27031 strain as disclosed herein, provided that the milk acidification kinetics of said mutant strain is according to the definitions given herein for any *Streptococcus thermophilus* strain of the invention, and in particular is similar to the milk acidification kinetics of the DSM deposited strains from which the mutants are derived from. In particular, the milk acidification kinetics of said mutant strain is characterized by:

a) an average speed of acidification between pH 6.00 and pH 5.30 which is at least $70 \times 10^{-4}$ UpH/min or equals $70 \times 10^{-4}$ UpH/min or is between $70 \times 10^{-4}$ and $250 \times 10^{-4}$, between $70 \times 10^{-4}$ and $200 \times 10^{-4}$, between $70 \times 10^{-4}$ and $180 \times 10^{-4}$, between $70 \times 10^{-4}$ and $140 \times 10^{-4}$, between $80 \times 10^{-4}$ and $120 \times 10^{-4}$, between $90 \times 10^{-4}$ and $110 \times 10^{-4}$, or between $95 \times 10^{-4}$ and $105 \times 10^{-4}$ UpH/min, and an average speed of acidification between pH 5.30 and pH 5.00 which is less than $22 \times 10^{-4}$ UpH/min or equals $22 \times 10^{-4}$ UpH/min or is between $1 \times 10^{-4}$ and $20 \times 10^{-4}$ between $2 \times 10^{-4}$ and $22 \times 10^{-4}$ between $2 \times 10^{-4}$ and $20 \times 10^{-4}$ between $5 \times 10^{-4}$ and $20 \times 10^{-4}$ or between $10 \times 10^{-4}$ and $18 \times 10^{-4}$ UpH/min; and/or b) a ratio of (1) average speed of acidification between pH 5.30 and pH 5.00 to (2) average speed of acidification between pH 6.00 and pH 5.30, which is less than or equals 25% or less than or equals 20%, less than or equals 18% or is between 1 and 25%, between 2 and 25%, between 5 and 18%, between 8 to 18% or between 10 and 18%, wherein preferably the average speed of acidification between pH 6.00 and pH 5.30 and the average speed of acidification between pH 5.30 and pH 5.00 are calculated as described in Assay I.

By a "mutant strain of the DSM 27029 strain, of the DSM 27030 strain, or of the DSM 27031 strain", it is meant a *S. thermophilus* strain whose genome is highly similar to the genome of the DSM 27029 strain, of the DSM 27030 strain, or of the DSM 27031 strain. Within the present application, said mutants are encompassed in the expression "*S. thermophilus* strain of the invention". The high similarity in terms of genome encompasses:

a *S. thermophilus* strain, the genome of which contains at most 150 mutational events as compared to the genome of the DSM 27029 strain, of the DSM 27030 strain, or of the DSM 27031 strain, preferably at most 140, at most 130, at most 120, at most 110, at most 100, 90, at most 80, at most 70, at most 60, at most 50, at most 40, at most 30, or at most 20 mutational events. A mutational event is defined as a SNP (single nucleotide polymorphism) or an INDEL (insertion, deletion, and combination thereof). The number of mutational events is determined by identifying the mutational events present in the mutant genome, as compared to the genome of the DSM 27029 strain, of the DSM 27030 strain, or of the DSM 27031 strain, each mutational event (SNP or INDEL) representing 1 mutational event (i.e., that for example an insertion of a sequence of several nucleotides is considered as one mutational event). In this context, the genome sequence of a mutant of the invention, defined by a number of mutational events as compared to the DSM 27029 strain, the DSM 27030 strain, or the DSM 27031 strain, may also be additionally defined by its percentage of identity with the genome sequence of the DSM 27029 strain, of the DSM 27030 strain, or of the DSM 27031 strain, wherein the percentage of identity represents herein the percentage of the genome sequence present in one strain and found in the other, in particular a) the percentage of the sequences present in the genome of the mutant strain and found in the genome of the DSM 27029 strain, of the DSM 27030 strain, or of the DSM 27031 strain, orb) the percentage of sequences present in the genome of the DSM 27029 strain, of the DSM 27030 strain, or of the DSM 27031 strain, and found in the mutant strain genome sequence. Thus, a mutant strain, differing from the DSM 27029 strain, the DSM 27030 strain, or the DSM 27031 strain only by insertion(s) or only by deletion(s) has a genome 100% identical to the genome of the DSM 27029 strain, the DSM 27030 strain, or the DSM 27031 strain, since the whole genome sequence of one strain is totally found in the genome sequence of the other. In a particular embodiment, the genome sequence of the mutant of the invention, defined by a number of mutational events, has an identity of at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% to the genome sequence of the DSM 27029 strain, of the DSM 27030 strain, or of the DSM 27031 strain, wherein the percentage of identity represents the percentage of the genome sequence present in one strain and found in the other; and/or a *S. thermophilus* strain, the genome sequence of which has an identity of at least 95%, with the genome sequence of the DSM 27029 strain, of the DSM 27030 strain, or of the DSM 27031 strain, in particular an identity of at least 90%, at least 91%, at least 95%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98%, or at least 99.99% with the genome sequence of the DSM 27029 strain, the DSM 27030 strain, or the DSM 27031 strain as deposited on Mar. 21, 2013. The identity is described in comparing the two genome sequences over their full-length (global alignment), and may be calculated using any program based on the Needleman-Wunsch algorithm.

It is noteworthy that the DSM 27029 strain, the DSM 27030 strain, and the DSM 27031 strain are mutants of each other, according to the definitions given above.

In a particular embodiment, the genome of said mutant strain comprises at least one element selected from the group consisting of a CRISPR4 locus, a CRISPR1 locus, and a CRISPR3 locus as defined above, in particular comprises one, two, or three elements selected from this group.

In a particular embodiment, the invention provides a *S. thermophilus* mutant strain of the DSM 27029 strain, of the DSM 27030 strain, or of the DSM 27031 strain as defined herein, wherein the genome of this mutant differs from the DSM 27029 strain, the DSM 27030 strain, or the DSM 27031 strain genome by its CRISPR4 locus, its CRISPR1 locus and/or its CRISPR3 locus, in particular by its CRISPR4 locus, in particular by its CRISPR1 locus, in particular by its CRISPR3 locus, in particular by its CRISPR4 locus and CRISPR1 locus, in particular by its CRISPR1 locus and CRISPR3 locus, in particular by its CRISPR4 locus and CRISPR3 locus, and in particular by its CRISPR4 locus, its CRISPR1 locus and its CRISPR3 locus. Said mutants, differing in one or several CRISPR loci (CRISPR1 and/or CRISPR3 and/or CRISPR4), are herein defined as CRISPR mutants of the DSM 27029 strain, of the DSM 27030 strain, or of the DSM 27031 strain.

In a particular embodiment, a *S. thermophilus* mutant of the DSM 27029 strain, of the DSM 27030 strain, or of the DSM 27031 strain, in particular a CRISPR mutant of the DSM 27029 strain, of the DSM 27030 strain, or of the DSM 27031 strain, is characterized by:

a CRISPR4 locus, comprising the sequence as defined in SEQ ID NO:3 or comprising part(s) of SEQ ID NO:3, such as defined in any embodiment described above; and/or a CRISPR1 locus, comprising the sequence as defined in SEQ ID NO:19 or comprising part(s) of SEQ ID NO:19, such as defined in any embodiment described above. In a particular embodiment, the CRISPR1 locus of this mutant consists of, from 5' to 3', at least one additional CRISPR1 [repeat-spacer] unit of sequence R1-X1, in particular at least 1, 2, 3, 4, 5, 6, 7, 8, 9, 10, 15, 20, 30 or more additional CRISPR1 [repeat-spacer] unit(s) of sequence R1-X1, and SEQ ID NO:19 (wherein R1 is as defined in SEQ ID NO:20, and X1 is any sequence with a length from 27 to 33 bp, in particular from 28 to 32 bp, in particular from 29 to 31 bp, and in particular exactly 30 bp). In another particular embodiment, the CRISPR1 locus of this mutant consists of, from 5' to 3', at least one additional CRISPR1 [repeat-spacer] unit of sequence R1X1, in particular at least 1, 2, 3, 4, 5, 6, 7, 8, 9, 10, 15, 20, 30 or more additional CRISPR1 [repeat-spacer] unit(s) of sequence R1-X1, at least 3 consecutive, in particular at least 3 consecutive terminal, CRISPR1 [repeat-spacer] units contained in SEQ ID NO:19 (part of SEQ ID NO:19), and the terminal repeat of SEQ ID NO:21; and/or a CRISPR3 locus, comprising the sequence as defined in SEQ ID NO:73 or comprising part(s) of SEQ ID NO:73, such as defined in any embodiment described above. In a particular embodiment, the CRISPR3 locus of this mutant consists of, from 5' to 3', at least one additional CRISPR1 [repeat-spacer] unit of sequence R3-X3, in particular at least or exactly 1, 2, 3, 4, 5, 6, 7, 8, 9, 10, 15, 20, 30 or more additional CRISPR3 [repeat-spacer] unit(s) of sequence R3-X3, and SEQ ID NO:73 (wherein R3 is as defined in SEQ ID NO:74, and X3 is any sequence with a length from 27 to 33 bp, in particular from 28 to 32 bp, in particular from 29 to 31 bp, and in particular exactly 30 bp). In another particular embodiment, the CRISPR3 locus of this mutant consists of, from 5' to 3', at least one additional CRISPR3 [repeat-spacer] unit of sequence R3-X3, in particular at least 1, 2, 3, 4, 5, 6, 7, 8, 9, 10, 15, 20, 30 or more additional CRISPR3 [repeat-spacer] unit(s) of sequence R3-X3, at least 3 consecutive, in particular at least 3 consecutive terminal, CRISPR3 [repeat-spacer] units contained in SEQ ID NO:73 (part of SEQ ID NO:73), and the terminal repeat of SEQ ID NO:74.

In a particular embodiment, the invention provides a *Streptococcus thermophilus* strain of the invention, wherein the milk acidification kinetics of said strain is characterized by:

a) an average speed of acidification between pH 6.00 and pH 5.30 which is at least $70 \times 10^{-4}$ UpH/min or equals $70 \times 10^{-4}$ UpH/min or is between $70 \times 10^{-4}$ and $250 \times 10^{-4}$, between $70 \times 10^{-4}$ and $200 \times 10^{-4}$ between $70 \times 10^{-4}$ and $180 \times 10^{-4}$ between $70 \times 10^{-4}$ and $140 \times 10^{-4}$ between $80 \times 10^{-4}$ and $120 \times 10^{-4}$, between $90 \times 10^{-4}$ and $110 \times 10^{-4}$, or between $95 \times 10^{-4}$ and $105 \times 10^{-4}$ UpH/min, and an average speed of acidification between pH 5.30 and pH 5.00 which is less than $22 \times 10^{-4}$ UpH/min or equals $22 \times 10^{-4}$ UpH/min or is between $1 \times 10^{-4}$ and $20 \times 10^{-4}$, between $2 \times 10^{-4}$ and $22 \times 10^{-4}$ between $2 \times 10^{-4}$ and $20 \times 10^{-4}$ between $5 \times 10^{-4}$ and $20 \times 10^{-4}$ or between $10 \times 10^{-4}$ and $18 \times 10^{-4}$ UpH/min; and/or b) a ratio of (1) average speed of acidification between pH 5.30 and pH 5.00 to (2) average speed of acidification between pH 6.00 and pH 5.30, which is less than or equals 25% or less than or equals 20%, less than or equals 18% or is between 1 and 25%, between 2 and 25%, between 5 and 18%, between 8 to 18% or between 10 and 18%, wherein preferably the average speed of acidification between pH 6.00 and pH 5.30 and the average speed of acidification between pH 5.30 and pH 5.00 are calculated as described in Assay I, and
wherein the *S. thermophilus* strain is not one or two of the following strains:
the DSM 27029 strain deposited on Mar. 21, 2013, at the Leibniz-Institut DSMZ,
the DSM 27030 strain deposited on Mar. 21, 2013, at the Leibniz-Institut DSMZ,
the DSM 27031 strain deposited on Mar. 21, 2013, at the Leibniz-Institut DSMZ.

In any embodiment, the *Streptococcus thermophilus* strain of the invention (including a *S. thermophilus* mutant strain as defined above) may be identified, starting from a group of *Streptococcus thermophilus* strains whose genome comprises a CRISPR4 locus as defined above, and/or comprises a CRISPR1 locus as defined above and/or comprises a CRISPR3 locus as defined above.

In a particular embodiment, the *Streptococcus thermophilus* strain of the invention, especially the mutant strain of the DSM 27029 strain, of the DSM 27030 strain, or of the DSM 27031 strain, is not the *Streptococcus salivarius thermophilus* strain deposited on May 6, 2011 at the Centraalbureau voor Schimmel-cultures (Fungal Biodiversity Centre, Utrecht, The Netherlands), under accession number CBS129457.

In a particular embodiment, the *Streptococcus thermophilus* strain of the invention, especially the mutant strain of the DSM 27029 strain, of the DSM 27030 strain, or of the DSM 27031 strain, is not the *Streptococcus salivarius thermophilus* strain deposited on May 6, 2011 at the Centraalbureau voor Schimmel-cultures, under accession number CBS129458.

In a particular embodiment, the *Streptococcus thermophilus* strain of the invention, especially the mutant strain of the DSM 27029 strain, of the DSM 27030 strain, or of the DSM 27031 strain, is neither the *Streptococcus salivarius thermophilus* strain deposited on May 6, 2011 at the Centraalbureau voor Schimmel-cultures under accession number CBS129457 nor the *Streptococcus salivarius thermophilus* strain deposited on May 6, 2011 at the Centraalbureau voor Schimmel-cultures, under accession number CBS129458.

The invention also provides a composition comprising or consisting of a culture of a *Streptococcus thermophilus* strain of the invention, in particular comprising or consisting of a culture of the *Streptococcus thermophilus* strain DSM 27029, a culture of the *Streptococcus thermophilus* strain DSM 27030, or a culture of the *Streptococcus thermophilus* strain DSM 27031, in particular comprising or consisting of a culture of a *Streptococcus thermophilus* mutant strain as defined above.

The composition of the invention, preferably when used as a starter culture, can be a pure culture or a mixed culture. Thus, a pure culture is defined as a culture wherein all or substantially all the culture consists of the same *Streptococcus thermophilus* strain of the invention. In the alternative, a mixed culture is defined as a culture comprising several microorganisms, in particular comprising several bacterial strains, including the *Streptococcus thermophilus* strain of the invention.

In a particular embodiment, the composition of the invention is or consists of a pure culture of a *Streptococcus thermophilus* strain as defined herein.

In another embodiment, the composition of the invention comprises, in addition to a culture of the *Streptococcus thermophilus* of the invention, at least one other microorganism. The term "microorganism" is defined herein as any organism that may be combined with the *Streptococcus thermophilus* of the invention, in particular for use in the preparation of products according to the invention. The term "microorganism" encompasses yeasts, molds, and bacteria, such as lactic acid bacteria species, a *Bifidobacterium* species, a *Brevibacterium* species, and/or a *Propionibacterium* species.

In a particular embodiment of mixed culture, the composition comprises, in addition to a culture of the *Streptococcus thermophilus* of the invention, at least one culture of lactic acid bacteria and/or at least one other culture of propionic bacteria. Suitable lactic acid bacteria include strains of a *Lactococcus* species, a *Streptococcus* species, a *Lactobacillus* species including *Lactobacillus acidophilus*, an *Enterococcus* species, a *Pediococcus* species, a *Leuconostoc* species, and an *Oenococcus* species or any combination thereof. *Lactococcus* species include *Lactococcus lactis*, including *Lactococcus lactis* subsp. *lactis*, *Lactococcus lactis* subsp. *lactis* biovar *diacetylactis*, and *Lactococcus lactis* subsp. *cremoris*. Other lactic acid bacteria species include *Leuconostoc* sp., *Streptococcus thermophilus*, *Lactobacillus delbrueckii* subsp. *bulgaricus*, and *Lactobacillus helveticus*.

Thus, the invention is also directed to, as a particular embodiment, a composition as defined herein comprising or consisting of a culture of the *Streptococcus thermophilus* of the invention, at least or exactly 1, 2, 3, 4, 5, 6, 7, 8, 9, or 10 strain(s) of the species *Streptococcus thermophilus*, different from the *S. thermophilus* strain of the invention, and/or a strain of the *Lactobacillus* species, and/or any combination thereof.

In a particular embodiment, the composition comprises or consists of a culture of the *Streptococcus thermophilus* of the invention, at least one, in particular at least or exactly 1, 2, 3, 4, 5, 6, 7, 8, 9, or 10 strain(s) of the species *Streptococcus thermophilus*, different from the *S. thermophilus* strain of the invention, and/or one or several strain(s) of the species *Lactobacillus delbrueckii* subsp. *bulgaricus*, and/or one or several strain(s) of the species *Lactobacillus helveticus* and/or any combination thereof. In a particular embodiment, the composition comprises or consists of a culture of the *Streptococcus thermophilus* of the invention, one strain of species *Streptococcus thermophilus*, different from the *S. thermophilus* strain of the invention, and a strain of the species *Lactobacillus delbrueckii* subsp. *bulgaricus*. In another particular embodiment, the composition comprises or consists of a culture of the *Streptococcus thermophilus* of the invention, two strains of the species *Streptococcus thermophilus*, both different from the *S. thermophilus* strain of the invention, and a strain of the species *Lactobacillus delbrueckii* sub sp. *bulgaricus*.

In a particular embodiment, the composition comprises or consists of a culture of the *Streptococcus thermophilus* of the invention, a *Lactococcus lactis* subsp. *lactis* and/or a *Lactococcus lactis* subsp. *cremoris*.

In a particular embodiment, the composition comprises or consists of a culture of the *Streptococcus thermophilus* of the invention and a complex mixed starter culture.

In a particular embodiment of any composition defined herein, either as a pure or mixed culture, the composition further comprises at least one probiotic strain such as *Bifidobacterium animalis* subsp. *lactis*, *Lactobacillus acidophilus*, *Lactobacillus paracasei*, or *Lactobacillus casei*.

In a particular embodiment, the composition as defined herein, either as a pure or mixed culture as defined above, further comprises, in particular food acceptable, component(s), such as, but not limited to, cryoprotective agents (or cryoprotectants), boosters and/or common additives. By "component", it is meant any molecule or solution which is not a microorganism as defined above. By way of example, cryoprotective agents include, cyclodextrin, maltitol, trehalose, sucrose, maltodextrine or combinations thereof. By way of example, boosters include nucleotides. By way of example, common additives include nutrients such as yeast extracts, sugars, and vitamins.

In a particular embodiment, the composition as defined herein, either as a pure or mixed culture as defined above, with or without additional component(s) is in a liquid, a frozen, or a dried-powder form, such as obtained after freeze-drying.

In a particular embodiment, the composition of the invention, either as a pure or mixed culture as defined above, with or without additional component(s), comprises the *S. thermophilus* strain of the invention (and optionally at least one other microorganism) in a concentrated form (concentrate), including frozen or dried concentrates. Thus, the concentration of the *S. thermophilus* strain of the invention within the composition is in the range of $10^5$ to $10^{12}$ CFU (colony forming units) per gram of the composition, preferably $10^7$ to $10^{12}$ CFU, and more preferably at least at least $10^7$, at least $10^8$, at least $10^9$, at least $10^{10}$ or at least $10^{11}$ CFU/g of the composition.

The invention also provides the use of a culture of a *Streptococcus thermophilus* strain of the invention or the use of a composition as defined herein, for preparing products, in particular food products or feed products, in particular fermented products, in particular fermented food products or fermented feed products. Thus, the invention also provides a method for preparing a product, preferably a food or feed product, wherein said method comprises a) putting a substrate into contact with or in the presence of a culture of the *S. thermophilus* strain of the invention or a composition as defined herein [or mixing a substrate with a culture of the *S. thermophilus* strain of the invention or a composition as defined herein], b) optionally fermenting said substrate, and c) obtaining said product. In a particular embodiment, the invention also provides a method for preparing a fermented product, preferably a fermented food or feed product, wherein said method comprises fermenting a substrate with or in the presence of a culture of the *S. thermophilus* strain of the invention or a composition as defined herein, and obtaining said fermented product.

The invention is also directed to any product, which is prepared from a *S. thermophilus* strain of the invention or a composition as defined herein, in particular by the methods disclosed herein, or which contains or comprises a *S. thermophilus* strain of the invention or a composition as defined herein. In a particular embodiment, the invention provides a product, in particular a food or a feed product, in particular a fermented product, in particular a fermented food or a fermented feed product, obtainable or obtained by methods as described herein. The invention also provides a product, in particular a food or a feed product, in particular a fermented product, in particular a fermented food or a fermented feed product, comprising a culture of the *S. thermophilus* strain of the invention or comprising a composition as defined herein.

Suitable products include, but are not limited to, a food, a foodstuff, a food ingredient, a food additive, a food supplement, a functional food, a feed, a nutritional supplement, or a probiotic supplement. According to the invention, by "food" it is meant a product that is intended for human consumption. According to the invention, by "feed" it is meant a product that is intended to feed an animal. As used herein the term "food ingredient" includes a formulation, which is or can be added to foods and includes formulations which can be used at low levels in a wide variety of products that require, for example, acidification. As used herein, the term "functional food" means a food which is capable of providing not only a nutritional effect and/or a taste satisfaction, but is also capable of delivering a further beneficial effect to the consumer. Suitable products include, but are not limited to, fruits, vegetables, fodder crops and vegetables including derived products, grain and grain-derived products, dairy foods and dairy food-derived products, meat, poultry, and seafood. The *S. thermophilus* strain of the invention or a composition as defined herein can be used in the preparation of food products such as one or more of confectionery products, dairy products, meat products, poultry products, fish products and bakery products. By way of example, the *S. thermophilus* strain of the invention or a composition as defined herein can be used as ingredients to a soft drink, a fruit juice or a beverage comprising whey protein, health tea, cocoa drink, milk drink and lactic acid bacteria drink, yoghurt, drinking yoghurt, and wine.

In a particular embodiment, the substrate into which the *S. thermophilus* strain of the invention or a composition as defined herein is added to [or mixed with] is milk substrate. Therefore, in a particular embodiment, the invention also provides the use of a culture of a *Streptococcus thermophilus* strain of the invention or the use of a composition as defined herein, for preparing a dairy product, in particular dairy food product or dairy feed product, in particular fermented dairy product, in particular fermented dairy food product or fermented dairy feed product. Thus, the invention also provides a method for preparing a dairy product, in particular dairy food product or dairy feed product, in particular fermented dairy product, in particular fermented dairy food product or fermented dairy feed product, wherein said method comprises a) putting into contact milk substrate with or in the presence of a culture of the *S. thermophilus* strain of the invention or with a composition as defined herein, b) optionally fermenting said milk substrate and c) obtaining said product. In a particular embodiment, the invention also provides a method for preparing a fermented dairy product, preferably fermented dairy food or feed product, wherein said method comprises fermenting milk substrate with or in the presence of a culture of the *S. thermophilus* strain of the invention or a composition as defined herein, and obtaining said fermented dairy product. In a particular embodiment, the milk substrate comprises solid items, such as fruits, chocolate products, or cereals. In a particular embodiment, the invention is also directed to the use of the *S. thermophilus* strain of the invention or any composition as defined herein (pure or mixed culture) to reduce the post-acidification phenomenon of the dairy product obtained with or of the dairy product fermented with or in presence of said *S. thermophilus* strain or said composition, as compared to dairy product(s) obtained without or fermented without or in the absence of the *S. thermophilus* strain of the invention, and directed to the dairy products per se. In a particular embodiment, the invention is also directed to the use of the *S. thermophilus* strain of the invention or any composition as defined herein (pure or mixed culture) to obtain a dairy product, in particular a yoghurt, whose pH is 4.4±0.1 and is stable when the dairy product is stored during 14 days at a positive temperature less than 10° C. In a particular embodiment, the invention is also directed to the use of the *S. thermophilus* strain of the invention or any composition as defined herein (pure or mixed culture) to obtain a dairy product, in particular a yoghurt, whose pH is 4.5±0.1 or is 4.4±0.05 when the dairy product is stored during 14 days at a positive temperature less than 10° C., and optionally whose pH is stable (i.e., within the same range) until 28 days.

By "milk substrate", it is meant milk of animal and/or plant origin. In a particular embodiment, the milk substrate is of animal origin, such as cow, goat, sheep, buffalo, zebra, horse, donkey, or camel, and the like. The milk may be in the native state, a reconstituted milk, a skimmed milk, or a milk supplemented with compounds necessary for the growth of the bacteria or for the subsequent processing of fermented milk, such as fat, proteins of a yeast extract, peptone and/or a surfactant, for example. In a particular embodiment, the milk substrate is commercial UHT milk (Ultra High Temperature treatment, i.e., 130° C. few seconds), in particular supplemented with 3% (w/w) of semi-skimmed milk powder, and pasteurized by heating, in particular during 10±1 min. at 90±0.2° C. In another embodiment, the milk substrate is of plant origin, i.e., is from extracts of plant material which have been treated or otherwise (vegetable milk), such as from leguminous plants (soya bean, chick pea, lentil and the like) or from oilseeds (colza, soya bean, sesame, cotton and the like), which extract contains proteins in solution or in colloidal suspension, which are coagulable by chemical action, by acid fermentation, and/or by heat. In another embodiment, the milk substrate is a mixture of animal milk(s) and of vegetable milk(s) as defined above.

Therefore, the invention provides a dairy product, in particular dairy food product or dairy feed product, in particular fermented dairy product, in particular fermented dairy food product or fermented dairy feed product, obtainable or obtained by methods as described herein with a milk substrate. The invention also provides a dairy product, in particular a fermented dairy product comprising a culture of the S. thermophilus strain of the invention or comprising a composition as defined herein. In a particular embodiment, the dairy product or fermented dairy product is or comprises a yoghurt, a cheese (such as an acid curd cheese, a hard cheese, a semi-hard cheese, a cottage cheese), a buttermilk, quark, a sour cream, kefir, a fermented whey-based beverage, a koumiss, a milk beverage, a yoghurt drink, a fermented milk, a matured cream, a fromage frais, a milk, a dairy product retentate, a processed cheese, a cottage cheese, a cream dessert, or infant milk, preferably based on a milk substrate of animal and/or plant origin.

EXPERIMENTAL

Example 1

Calculation of Average Speed of Acidification Between pH 6.00 and pH 5.30 (S1), Average Speed of Acidification Between pH 5.30 and pH 5.00 (S2) and S2/S1 Ratio Assay I Commercial half-fat UHT cow-milk (fat 1.5% w/w) ["Le Petit Vendéen"; GLAC—France] is supplemented with 3% (W/W) skimmed milk powder. After dissolution, the mix is heat treated at 90° C. for 10 min. The heating step from 20-25° C. to 90° C. lasts no more than 35 min and the cooling step from 90° C. to 35° C.-45° C. lasts no more than 45 min. Just before inoculation, 1 g/100 L (w/v) of sodium formiate is added. The inoculation is performed with strains preserved at −80° C. in milk based medium. The inoculation rate is 1×10$^6$ CFU/ml of milk-base. The incubation temperature is set at 43° C.+/−1° C., and kept constant in a water bath during the fermentation. A Cinac system (CINAC, an automated system for control of lactic starters; Corrieu G, Picque D, Perret B, Quemener P; Process Magazine; 1992; no. 1068; p. 24-27) was used for online measurement of pH change. The pH is recorded each 5 min during 24 h, and summarized in a table or presented as a CINAC curve.

The 3 following parameters are determined: time for pH=6.00 ($T_{pH6.00}$), time for pH=5.30 ($T_{pH5.30}$) and time for pH=5.00 ($T_{pH5.00}$). These parameters are obtained directly by the online recording, or when the time to obtain the targeted pH is not present in the table, a linear interpolation is done between the two recorded data (see example with strain DGCC7984 below).

Finally, the following parameters are defined, to describe the milk acidification kinetics:

$S_1=(6.00-5.30)/(T_{pH5.30}-T_{pH6.00})$ (UpH/min) [average speed of acidification between pH 6.00 and pH 5.30];

$S2=(5.30-5.00)/(T_{pH5.00}-T_{pH5.30})$ (UpH/min) [average speed of acidification between pH 5.30 and pH 5.00]; and the ratio of S2 to S1 [S2/S1 ratio] (in percentage).

Implementation to the Strain DGCC7984

The Assay I (as described above) has been implemented in the strain DGCC7984. The pH, recorded each 5 min during 24 h, is disclosed in Table 1.

The 3 parameters, 1) time for pH=6.00 ($T_{pH6.00}$), 2) time for pH=5.30 ($T_{pH5.30}$), and 3) time for pH=5.00 ($T_{pH5.00}$), have been determined.

Thus, time for pH=5.30 has been obtained directly by the on line recording (235 min). Since time for pH=6.00 and time for pH=5.00 ($T_{pH5.00}$) have not been found in the Table, a linear interpolation has been done between the two recorded data surrounding pH=6.00 and the two recorded data surrounding pH=5.00, by the method as follow (here is the example for the evaluation of $T_{pH6.00}$). The same mode of calculation is used for the evaluation of $T_{pH5.00}$.

$$T_{pH6.00}=(6.00-pH_1+T_1*((pH_1-pH_2)/(T_1-T_2)))/((pH_1-pH_2)/(T_1-T_2))$$

In the example, $T_1=175$ min for $pH_1=6.04$, and $T_2=180$ min for $pH_2=5.99$ $$T_{pH6.00}=(6.00-6.04+175*((6.04-5.99)/(175-180)))/((6.04-5.99)/(175-180))$$

$$T_{pH6.00}=(6.00-6.04+175*((0.05/5)))/(0.05/5)$$

$$T_{pH6.00}=0.04+(175*0.01)/0.01=179 \text{ min.}$$

TABLE 1

| Time (min) | pH |
| --- | --- |
| 0 | 6.45 |
| 5 | 6.44 |
| 10 | 6.44 |
| 15 | 6.43 |
| 20 | 6.42 |
| 25 | 6.42 |
| 30 | 6.41 |
| 35 | 6.41 |
| 40 | 6.41 |
| 45 | 6.41 |
| 50 | 6.41 |
| 55 | 6.41 |
| 60 | 6.40 |
| 65 | 6.40 |
| 70 | 6.39 |
| 75 | 6.39 |
| 80 | 6.38 |
| 85 | 6.37 |

TABLE 1-continued

| Time (min) | pH |
|---|---|
| 90 | 6.36 |
| 95 | 6.35 |
| 100 | 6.33 |
| 105 | 6.32 |
| 110 | 6.30 |
| 115 | 6.29 |
| 120 | 6.27 |
| 125 | 6.25 |
| 130 | 6.24 |
| 135 | 6.22 |
| 140 | 6.21 |
| 145 | 6.19 |
| 150 | 6.18 |
| 155 | 6.16 |
| 160 | 6.14 |
| 165 | 6.11 |
| 170 | 6.08 |
| 175 | 6.04 |
| 180 | 5.99 |
| 185 | 5.93 |
| 190 | 5.87 |
| 195 | 5.80 |
| 200 | 5.73 |
| 205 | 5.66 |
| 210 | 5.59 |
| 215 | 5.52 |
| 220 | 5.46 |
| 225 | 5.40 |
| 230 | 5.35 |
| 235 | 5.30 |
| 240 | 5.25 |
| 245 | 5.21 |
| 250 | 5.18 |
| 255 | 5.14 |
| 260 | 5.11 |
| 265 | 5.08 |
| 270 | 5.06 |
| 275 | 5.03 |
| 280 | 5.01 |
| 285 | 4.99 |
| 290 | 4.97 |
| 295 | 4.95 |
| 300 | 4.93 |
| 305 | 4.91 |
| 310 | 4.89 |
| 315 | 4.87 |
| 320 | 4.86 |
| 325 | 4.84 |
| 330 | 4.82 |
| 335 | 4.81 |
| 340 | 4.80 |
| 345 | 4.78 |
| 350 | 4.77 |
| 355 | 4.76 |
| 360 | 4.75 |
| 365 | 4.73 |
| 370 | 4.72 |
| 375 | 4.71 |
| 380 | 4.70 |
| 385 | 4.69 |
| 390 | 4.68 |
| 395 | 4.67 |
| 400 | 4.66 |
| 405 | 4.65 |
| 410 | 4.65 |
| 415 | 4.64 |
| 420 | 4.63 |
| 425 | 4.62 |
| 430 | 4.61 |
| 435 | 4.60 |
| 440 | 4.60 |
| 445 | 4.59 |
| 450 | 4.58 |
| 455 | 4.58 |
| 460 | 4.57 |
| 465 | 4.56 |
| 470 | 4.56 |
| 475 | 4.55 |
| 480 | 4.54 |
| 485 | 4.54 |
| 490 | 4.53 |
| 495 | 4.53 |
| 500 | 4.52 |
| 505 | 4.51 |
| 510 | 4.51 |
| 515 | 4.50 |
| 520 | 4.50 |
| 525 | 4.49 |
| 530 | 4.49 |
| 535 | 4.48 |
| 540 | 4.48 |
| 545 | 4.48 |
| 550 | 4.47 |
| 555 | 4.47 |
| 560 | 4.46 |
| 565 | 4.46 |
| 570 | 4.45 |
| 575 | 4.45 |
| 580 | 4.45 |
| 585 | 4.44 |
| 590 | 4.44 |
| 595 | 4.43 |
| 600 | 4.43 |
| 605 | 4.43 |
| 610 | 4.42 |
| 615 | 4.42 |
| 620 | 4.42 |
| 625 | 4.41 |
| 630 | 4.41 |
| 635 | 4.41 |
| 640 | 4.40 |
| 645 | 4.40 |
| 650 | 4.40 |
| 655 | 4.39 |
| 660 | 4.39 |
| 665 | 4.39 |
| 670 | 4.38 |
| 675 | 4.38 |
| 680 | 4.38 |
| 685 | 4.38 |
| 690 | 4.37 |
| 695 | 4.37 |
| 700 | 4.37 |
| 705 | 4.37 |
| 710 | 4.36 |
| 715 | 4.36 |
| 720 | 4.36 |
| 725 | 4.36 |
| 730 | 4.35 |
| 735 | 4.35 |
| 740 | 4.35 |
| 745 | 4.35 |
| 750 | 4.35 |
| 755 | 4.34 |
| 760 | 4.34 |
| 765 | 4.34 |
| 770 | 4.34 |
| 775 | 4.34 |
| 780 | 4.33 |
| 785 | 4.33 |
| 790 | 4.33 |
| 795 | 4.33 |
| 800 | 4.33 |
| 805 | 4.33 |
| 810 | 4.32 |
| 815 | 4.32 |
| 820 | 4.32 |
| 825 | 4.32 |
| 830 | 4.32 |
| 835 | 4.32 |
| 840 | 4.31 |
| 845 | 4.31 |
| 850 | 4.31 |
| 855 | 4.31 |
| 860 | 4.31 |
| 865 | 4.31 |

TABLE 1-continued

| Time (min) | pH |
|---|---|
| 870 | 4.31 |
| 875 | 4.30 |
| 880 | 4.30 |
| 885 | 4.30 |
| 890 | 4.30 |
| 895 | 4.30 |
| 900 | 4.30 |
| 905 | 4.30 |
| 910 | 4.30 |
| 915 | 4.30 |
| 920 | 4.29 |
| 925 | 4.29 |
| 930 | 4.29 |
| 935 | 4.29 |
| 940 | 4.29 |
| 945 | 4.29 |
| 950 | 4.29 |
| 955 | 4.29 |
| 960 | 4.28 |
| 965 | 4.28 |
| 970 | 4.28 |
| 975 | 4.28 |
| 980 | 4.28 |
| 985 | 4.28 |
| 990 | 4.28 |
| 995 | 4.28 |
| 1000 | 4.28 |
| 1005 | 4.28 |
| 1010 | 4.27 |
| 1015 | 4.27 |
| 1020 | 4.27 |
| 1025 | 4.27 |
| 1030 | 4.27 |
| 1035 | 4.27 |
| 1040 | 4.27 |
| 1045 | 4.27 |
| 1050 | 4.27 |
| 1055 | 4.27 |
| 1060 | 4.27 |
| 1065 | 4.26 |
| 1070 | 4.26 |
| 1075 | 4.26 |
| 1080 | 4.26 |
| 1085 | 4.26 |
| 1090 | 4.26 |
| 1095 | 4.26 |
| 1100 | 4.26 |
| 1105 | 4.26 |
| 1110 | 4.26 |
| 1115 | 4.26 |
| 1120 | 4.26 |
| 1125 | 4.25 |
| 1130 | 4.25 |
| 1135 | 4.25 |
| 1140 | 4.25 |
| 1145 | 4.25 |
| 1150 | 4.25 |
| 1155 | 4.25 |
| 1160 | 4.25 |
| 1165 | 4.25 |
| 1170 | 4.25 |
| 1175 | 4.25 |
| 1180 | 4.25 |
| 1185 | 4.25 |
| 1190 | 4.24 |
| 1195 | 4.24 |
| 1200 | 4.24 |
| 1205 | 4.24 |
| 1210 | 4.24 |
| 1215 | 4.24 |
| 1220 | 4.24 |
| 1225 | 4.24 |
| 1230 | 4.24 |
| 1235 | 4.24 |
| 1240 | 4.24 |
| 1245 | 4.24 |
| 1250 | 4.24 |
| 1255 | 4.24 |
| 1260 | 4.24 |
| 1265 | 4.24 |
| 1270 | 4.24 |
| 1275 | 4.23 |
| 1280 | 4.23 |
| 1285 | 4.23 |
| 1290 | 4.23 |
| 1295 | 4.23 |
| 1300 | 4.23 |
| 1305 | 4.23 |
| 1310 | 4.23 |
| 1315 | 4.23 |
| 1320 | 4.23 |
| 1325 | 4.23 |
| 1330 | 4.23 |
| 1335 | 4.23 |
| 1340 | 4.23 |
| 1345 | 4.23 |
| 1350 | 4.23 |
| 1355 | 4.23 |
| 1360 | 4.23 |
| 1365 | 4.22 |
| 1370 | 4.22 |
| 1375 | 4.22 |
| 1380 | 4.22 |
| 1385 | 4.22 |
| 1390 | 4.22 |
| 1395 | 4.22 |
| 1400 | 4.22 |
| 1405 | 4.22 |
| 1410 | 4.22 |
| 1415 | 4.22 |
| 1420 | 4.22 |
| 1425 | 4.22 |
| 1430 | 4.22 |
| 1435 | 4.22 |
| 1440 | 4.22 |

Finally, S1, S2, and S2/S1 ratio for the strain DGCC7984 have been calculated and are reported in Table 2:

TABLE 2

| | |
|---|---|
| $T_{pH\ 6.00}$ (min) | 179 |
| $T_{pH\ 5.30}$ (min) | 235 |
| $T_{pH\ 5.00}$ (min) | 282.5 |
| $S_1 = (6.00 - 5.30)/(T_{pH\ 5.30} - T_{pH\ 6.00})$ (UpH/min.) | 0.0125 |
| $S_2 = (5.30 - 5.00)/(T_{pH\ 5.00} - T_{pH\ 5.30})$ (UpH/min.) | 0.0063 |
| R (%) | 50 |

Example 2

Determination of S1, S2, and S2/S1 Ratio for 69 *Streptococcus thermophilus* Strains Strains 69 *Streptococcus thermophilus* strains from the Dupont Collection have been used. From these 69 strains, 7 *S. thermophilus* strains have been previously disclosed in patent applications and deposited at the C.N.C.M., and 2 *S. thermophilus* strains have their genome sequence available in the NCBI database.

The information about these 9 strains is summarized below:
  (1) DGCC 7809 strain: deposited at the C.N.C.M, under number 1-2425
  (2) DGCC7710 strain: deposited at the C.N.C.M, under number 1-2423
  (3) DGCC8014 strain: deposited at the C.N.C.M, under number 1-3617

(4) DGCC7984 strain: deposited at the C.N.C.M, under number 1-2980
(5) DGCC7666 strain: deposited at the C.N.C.M, under number 1-3782
(6) DGCC7681 strain: deposited at the C.N.C.M, under number 1-2432
(7) DGCC7891 strain: deposited at the C.N.C.M, under number 1-2429
(8) DGCC3198 strain: LMD-9, genome sequence available from NCBI, accession NC_008532.1
(9) DGCC9742 strain: LMG 18311, genome sequence available from NCBI, accession NC_006448.1

Herein, DGCC numbers are internal references to DuPont collection; DSM and CNCM numbers are the numbers assigned respectively by the Leibniz-Institut DSMZ-Deutsche Sammlung von Mikroorganismen und Zellkulturen, GmbH, and the Collection Nationale de Cultures de Microorganismes (Paris, France), following deposit under the Budapest Treaty.

Determination of S1, S2, and S2/S1 Ratio for 69 *Streptococcus thermophilus* Strains The Assay I (as described above) has been implemented for the 69 *Streptococcus thermophilus* strains, and the S1 value, S2 value and S2/S1 ratio calculated as described above.

Results and Comments

The average speed of acidification between pH 6.00 and pH 5.30 (51) and the average speed of acidification between pH 5.30 and pH 5.00 (S2) for 69 *Streptococcus thermophilus* strains have been determined, and the S2/S1 ratio calculated. The 69 *Streptococcus thermophilus* strains have been sorted from the smallest to the largest S1 values (Table 3).

One can observe that the higher the S1 value of a *S. thermophilus* strain, the higher its S2 value. Briefly, *S. thermophilus* strains having a low S1 value (less than $70 \times 10^{-4}$ UpH/min) have a S2 value less than $30 \times 10^{-4}$ UpH/min, and strains having a high S1 value (at least $70 \times 10^{-4}$ UpH/min) have a S2 value of at least $35 \times 10^{-4}$ UpH/min. This is clearly visible from FIG. 1 which represents the S2 value of a strain as a function of its S1 value (grey diamonds).

Surprisingly, 3 strains have atypical milk acidification kinetics, i.e., have a high S1 value (at least $70 \times 10^{-4}$ UpH/min), while at the same time having a S2 value less than $22 \times 10^{-4}$ UpH/min (even lower than the S2 value of some strains having a low S1 value). These strains, deposited as DSM 27029 strain, DSM 27030 strain, or DSM 27031 strain [under the Budapest Treaty on Mar. 21, 2013 at the Leibniz-Institut DSMZ-Deutsche Sammlung von Mikroorganismen und Zellkulturen, GmbH], present a S2 value which is unlinked to the S1 value, as can be shown in FIG. 1 (black squares).

This difference in acidification kinetics between the tested *S. thermophilus* strains can also be put in evidence by calculating the ratio of S2 value to S1 value (in %). Thus, generally *S. thermophilus* strains having a low S1 value (less than $70 \times 10^{-4}$ UpH/min) have a S2/S1 ratio between 30 and 50%, and strains having a S1 value of at least $70 \times 10^{-4}$ UpH/min have a S2/S1 ratio of at least 45 and up to 70%.

In contrast, the 3 DSM 27029, DSM 27030 and DSM 27031 strains have, despite their high S1 value (at least $70 \times 10^{-4}$ UpH/min), a S2/S1 ratio which is less than 25%, i.e., which is the lowest S2/S1 ratio of all the tested *S. thermophilus* strains. More surprisingly, the S2/S1 ratio of these 3 strains is between twice less and 6 times less the S2/S1 ratio of *S. thermophilus* strains having a S1 value of at least $70 \times 10^{-4}$ UpH/min.

TABLE 3 average speed of acidification between pH 6.00 and pH 5.30 [S1(6.0-5.3), in $10^{-4}$ UpH/min], average speed of acidification between pH 5.30 and pH 5.00 [S2(5.3-5.0) in $10^{-4}$ UpH/min] and S2/S1 ratio (in %) for 69 *Streptococcus thermophilus* strains; sorted from the smallest to the largest S1 values; [1] to [9] refer to the strains (1) to (9) discussed above.

| Ref | S1 (6.0-5.3) | S2 (5.3-5.0) | S2/S1 (%) |
|---|---|---|---|
| DGCC2058 | 16 | 6 | 38 |
| DGCC2141 | 25 | 9 | 36 |
| DGCC7785 | 30 | 10 | 34 |
| DGCC9742[9] | 30 | 14 | 47 |
| DGCC8178 | 30 | 13 | 42 |
| DGCC8400 | 33 | 12 | 37 |
| DGCC7891[7] | 34 | 13 | 39 |
| DGCC7722 | 35 | 14 | 39 |
| DGCC7666[5] | 36 | 14 | 41 |
| DGCC8413 | 37 | 18 | 48 |
| DGCC7773 | 40 | 15 | 38 |
| DGCC7967 | 40 | 13 | 33 |
| DGCC938 | 40 | 15 | 38 |
| DGCC7681[6] | 45 | 18 | 40 |
| DGCC7790 | 46 | 16 | 35 |
| DGCC47 | 46 | 13 | 27 |
| DGCC8836 | 49 | 16 | 33 |
| DGCC7873 | 52 | 21 | 40 |
| DGCC8837 | 52 | 18 | 35 |
| DGCC757 | 53 | 30 | 57 |
| DGCC7856 | 55 | 23 | 41 |
| DGCC2057 | 64 | 33 | 52 |
| DGCC7700 | 64 | 29 | 45 |
| DGCC8854 | 70 | 43 | 61 |
| DGCC8849 | 74 | 24 | 33 |
| DGCC782 | 78 | 55 | 70 |
| DGCC8006 | 81 | 61 | 75 |
| DGCC8014[3] | 81 | 48 | 59 |
| DGCC7992 | 81 | 35 | 43 |
| DGCC7710[2] | 93 | 56 | 60 |
| DGCC8846 | 93 | 46 | 49 |
| DSM27031 | 98 | 16 | 16 |
| DSM27029 | 98 | 11 | 11 |
| DGCC7809[1] | 102 | 65 | 64 |
| DGCC2062 | 103 | 57 | 55 |
| DSM27030 | 103 | 16 | 16 |
| DGCC8900 | 115 | 59 | 51 |
| DGCC8853 | 119 | 73 | 62 |
| DGCC3198[8] | 122 | 62 | 51 |
| DGCC1351 | 123 | 63 | 51 |
| DGCC7984[4] | 125 | 63 | 50 |
| DGCC8759 | 127 | 67 | 52 |
| DGCC8901 | 127 | 63 | 49 |
| DGCC8771 | 130 | 73 | 56 |
| DGCC8009 | 135 | 91 | 68 |
| DGCC8776 | 135 | 77 | 57 |
| DGCC8773 | 135 | 70 | 52 |
| DGCC8897 | 139 | 72 | 52 |
| DGCC8857 | 140 | 70 | 50 |
| DGCC8787 | 141 | 86 | 61 |
| DGCC8851 | 149 | 91 | 61 |
| DGCC8905 | 152 | 86 | 56 |
| DGCC8833 | 156 | 81 | 52 |
| DGCC8782 | 159 | 97 | 61 |
| DGCC2056 | 159 | 75 | 47 |
| DGCC8904 | 159 | 75 | 47 |
| DGCC1974 | 163 | 79 | 48 |
| DGCC8011 | 167 | 107 | 64 |
| DGCC8832 | 167 | 100 | 60 |
| DGCC8855 | 167 | 91 | 55 |
| DGCC8906 | 171 | 107 | 63 |
| DGCC959 | 171 | 95 | 56 |
| DGCC8835 | 175 | 120 | 69 |
| DGCC8751 | 175 | 86 | 49 |
| DGCC7854 | 185 | 110 | 59 |
| DGCC7919 | 197 | 100 | 51 |
| DGCC7796 | 201 | 106 | 53 |
| DGCC8848 | 206 | 130 | 63 |
| DGCC8828 | 226 | 125 | 55 |

Figure 2:
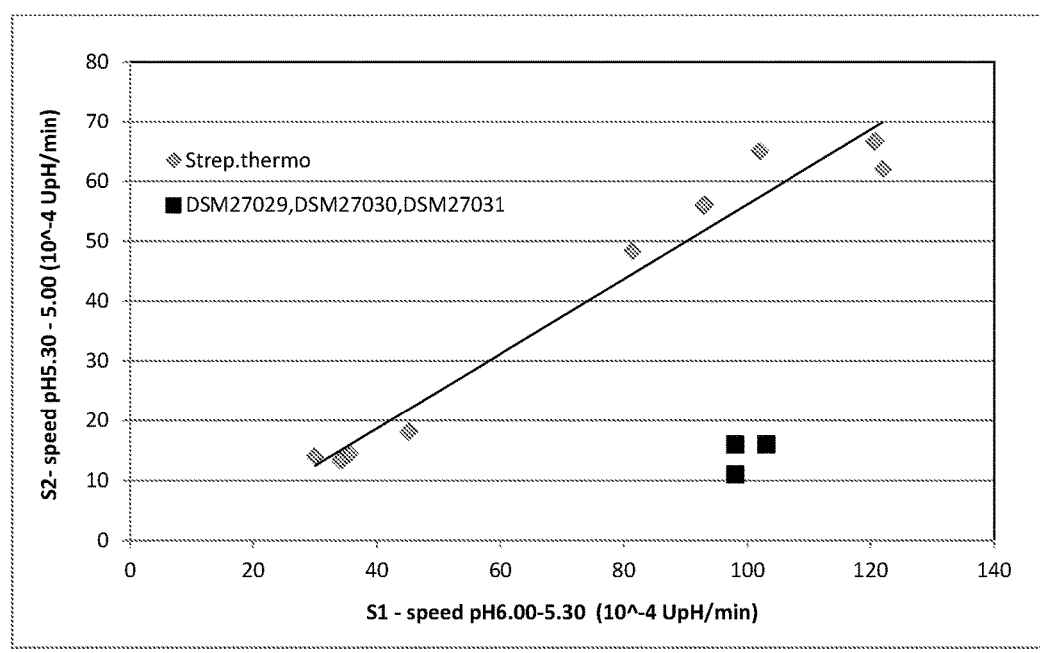
FIG. 2: (A) average speed of acidification between pH 5.30 and pH 5.00 (S2) as a function of the average speed of acidification between pH 6.00 and pH 5.30 (S1), for 9 known *S. thermophilus* strains (grey diamonds) and 3 strains of the invention (black squares); (B) S2/S1 ratio (in %) for the 12 *S. thermophilus* strains of (A) above.
Figure 2:
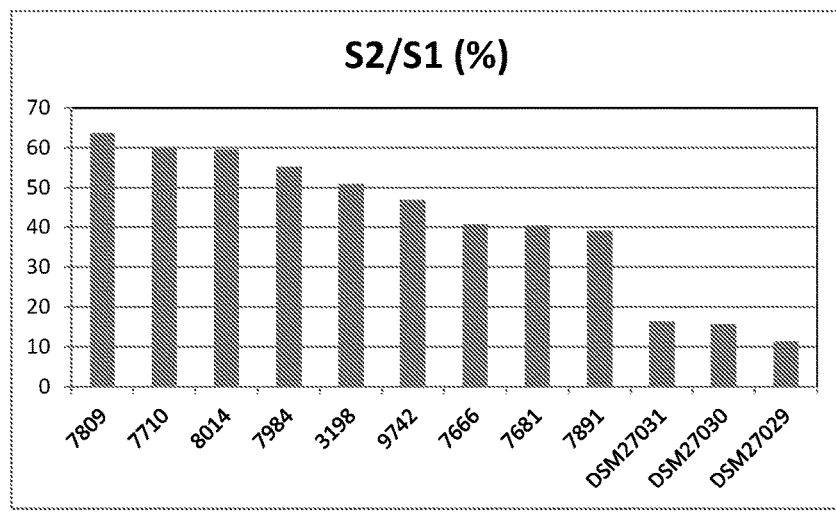

The average speed of acidification between pH 6.00 and pH 5.30 (S1), the average speed of acidification between pH 5.30 and pH 5.00 (S2) and the S2/S1 ratio of these 3 strains have been more specifically compared with the ones of the 9 *S. thermophilus* strains identified under (1) to (9) above. Thus, the unlink between the S2 and S1 values as well as the low ratio S2/S1 are clearly apparent in FIGS. 2A and 2B as compared to the 9 other strains.

Consequently, these 3 strains present atypical milk acidification kinetics with a low S2/S1 ratio, in particular if we consider that their S1 value is at least $70 \times 10^{-4}$ UpH/min.

Example 3

Genetic Analysis of the DSM 27029, DSM 27030, and DSM 27031 Strains, CRISPR Mutants, and Determination of S1, S2 and S2/S1 Ratio Genetic Analysis Several regions of the genome of the DSM 27029, DSM 27030, and DSM 27031 strains have been analysed. Thus, the sequence of the CRISPR4 locus, the sequence of the CRISPR1 locus, and the sequence of the CRISPR3 locus have been determined.

In the 3 deposited DSM strains, the CRISPR4 locus consists of the sequence as defined in SEQ ID NO:3 and comprises 12 CRISPR4 [repeat-spacer] units. It is flanked by the CRISPR4 leader as defined in SEQ ID NO:2 and the CRISPR4 trailer as defined in SEQ ID NO:1.

In the 3 deposited DSM strains, the CRISPR1 locus consists of the sequence as defined in SEQ ID NO:19, and comprises 32 CRISPR1 [repeat-spacer] units. It is flanked by the CRISPR1 leader as defined in SEQ ID NO:17 and the CRISPR1 trailer as defined in SEQ ID NO:18 In the 3 deposited DSM strains, the CRISPR3 locus consists of the sequence as defined in SEQ ID NO:73, and comprises 12 CRISPR3 [repeat-spacer] units. It is flanked by the CRISPR3 leader as defined in SEQ ID NO:71 and the CRISPR3 trailer as defined in SEQ ID NO:72.

CRISPR Mutants

Several CRISPR mutants of the deposited strains have been obtained. Phage challenge, described in details in patent application WO2008/108989, may be used to obtain CRISPR mutants of the invention.

Determination of S1, S2, and S2/S1 Ratio of CRISPR Mutants

As an example of the several CRISPR mutants obtained, two CRISPR mutants of strain DSM 27029 have been characterized, for their S1 value, S2 value and S2/S1 ratio.

The first DSM 27029 CRISPR mutant (DSM 27029 M1) has a S1 value of $104 \times 10^{-4}$ UpH/min, a S2 value of $18 \times 10^{-4}$ UpH/min and a S2/S1 ratio of 17%. The second DSM 27029 CRISPR mutant (DSM 27029 M2) has a S1 value of $112 \times 10^{-4}$ UpH/min, a S2 value of $23 \times 10^{-4}$ UpH/min and a S2/S1 ratio of 20%.

These data confirm that the CRISPR mutants conserve the atypical milk acidification kinetics (i.e., a S1 value of at least $70 \times 10^{-4}$ UpH/min, a S2 value less than $22 \times 10^{-4}$ UpH/min, and/or a S2/S1 ratio less than 25%). These data also confirm that the different CRISPR loci as defined herein, taken alone or in combination, may guide the person skilled in the art in the identification of *S. thermophilus* strains of the invention.

Example 4

Preparation of Fermented Milks Using Strain DSM 27029

Preparation of Fresh Fermented Milks Fermented milks have been prepared according to the following experimental conditions:

Preparation of the Milk Base:

Commercial half-fat UHT milk (fat 1.5% w/w)+3% skimmed milk powder was heat treated at 90° C. for 10 min. Just before inoculation, 1 g/100 L (w/v) of sodium formiate was added.

Inoculation:

The inoculation was performed with strains preserved at −80° C. in milk based medium. The strain DSM 27029 was combined with a second *Streptococcus thermophilus* strain, DGCC2057, and a strain belonging to *Lactobacillus delbrueckii* subsp. *bulgaricus*, DGCC10697. Inoculation rates were adjusted at $8 \times 10^5$ CFU/ml, $2 \times 10^5$ CFU/ml, and $1 \times 10^4$ CFU/ml of milk-base, respectively. A starter YOMIX™ 465 LYO was used for reference, and inoculated at commercial dosage of 20 DCU/100 L.

Fermentation:

The incubation temperature was set at 43° C.+/−1° C., and kept constant in a water bath during the fermentation. A Cinac system (CINAC, an automated system for control of lactic starters; Corrieu G, Picque D, Perret B, Quemener P; Process Magazine; 1992; no. 1068; p. 24-27) was used for on-line measurement of pH change. At pH 4.60+/−0.1, the fermented product was cooled down to 6° C., and then stored at 6° C. Time to achieve a pH 4.60 (at which the product is cooled down from 43° C. to 6° C.) was calculated.

Fresh Fermented Milks Feature Evaluation Methods.

Fresh fermented milk can be described by its texture and flavour attributes. This evaluation has been performed after storage of the fresh fermented milks during 14 days at 6° C. For texture, rheological tools have been used. The viscosity of the milk fermented was measured by using a Brookfield viscometer (Brookfield Engineering laboratories, Inc.) equipped with a helipath stand. Then, the following steps have been performed.

equipping said viscometer with a T-bar spindle type C,
filling a 125 mL glass yogurt pot with the fermented milk,
introducing the yogurt pot filled with the fermented milk in the viscometer,
applying a speed of 10 rpm to the viscometer, and then reading, after 30 seconds of rotation, the viscosity of the sample.

Furthermore, a Capillary Break-up Extensional Rheometer (CaBER 1 from HAAKE, THERMO ELECTRON Corp.) has been used for assessing the extensibility of the fresh fermented milk. The protocol to evaluate the break up time is briefly described below.

warming a sample of the fermented milk to 20° C.,
breaking and homogenizing the gel by stirring 20 times with a standard plastic spoon,
placing 604, of the homogenized fermented milk between two plates of a Capillary Break-up Extensional Rheometer (CaBER 1 from HAAKE, THERMO ELECTRON Corp.) having the following settings: plate diameter: 6 mm; initial height: 2 mm; final height: 9.65 mm; strike speed: 0.24 mm/ms (Strike time: 40 ms);

laser-micrometer: class 1 laser operating in the infrared and having a resolution of 10 μm.

measuring the Relative Break-up Time of the sample.

The sensory tasting sessions involved 3 specialist assessors. These assessors were asked to evaluate the products in blind test conditions (the fermented milks were coded). Six different sensory attributes were assessed: the "cut", the "thickness with spoon", the "ropiness", the "thickness in mouth", the "stickiness in mouth" and the "acidity". Each attribute was quoted with a range between "0" and "4".

Results and Comments

In order to achieve a pH 4.60, the YOMIX starter needs 375 min and the blend of strains (comprising strain DSM 27029) needs 437 min. Both are usual technological times to produce fermented milk at this temperature.

The fresh fermented milk features obtained with the co-inoculation of different strains and the commercial YOMIX culture are reported in Tables 4 and 5:

TABLE 4

Comparison between fresh fermented milks prepared with the blend of DSM 27029/DGCC2057/DGCC10697 and prepared with a commercial culture YOMIX ™ 465 (YOMIX).

|  | Viscosity (Pa · s) | Relative Breakup Time (ms) |
| --- | --- | --- |
| blend | 65.5 | 99.3 |
| YOMIX | 56.8 | 46.0 |

It can be noticed that the viscosity and the relative break up time of the fresh fermented milk prepared with the blend is significantly higher than the ones measured for the fresh fermented milk prepared with YOMIX.

TABLE 5

Quotation of several sensory attributes for fresh fermented milk prepared with the blend and YOMIX starter cultures.

|  | cut | thickness with spoon | ropiness | thickness in mouth | stickiness | acidity |
| --- | --- | --- | --- | --- | --- | --- |
| blend | 1.0 | 4.0 | 3.0 | 4.0 | 3.0 | 0.0 |
| YOMIX | 3.0 | 2.5 | 0.5 | 2.5 | 1.0 | 0.0 |

For the yoghurt prepared with the blend, the "cut" is significantly lower than for the yoghurt prepared with YOMIX. This feature can be of interest for stirred yoghurt production. The "thickness in spoon" and "thickness in mouth" is significantly higher for the yoghurt prepared with the blend compared to the yoghurt prepared with YOMIX. This result is valuable for stirred yoghurt technology. Results clearly suggest that strain DSM 27029, combined with other strains, can help yoghurt producers to offer products with very high texture quality to the final consumers.

Therefore, it can be concluded that using DSM 27029 as part of the inoculum provides yoghurt with features of interest for fresh fermented milks producers.

Example 5

Preparation of Fermented Milks Using Strain DSM 27030

Preparation of Fresh Fermented Milks

Fermented milks have been prepared according to example 4, regarding the preparation of milk base and fermentation conditions. The inoculation was performed with strains preserved at −80° C. in milk-based medium. The strain DSM 27030 was combined with a second *Streptococcus thermophilus* strain, DGCC2057, and a strain belonging to *Lactobacillus delbrueckii* subsp. *bulgaricus*, DGCC10697. Inoculation rates were adjusted at 8×10$^5$ CFU/ml, 2×10$^5$ CFU/ml, and 1×10$^4$ CFU/ml of milk-base, respectively. A starter YOMIX™ 465 LYO was used for reference. It was inoculated at commercial dosage of 20 DCU/100 L. Fermentation was carried out in 125 ml yoghurt pot filled with 110 ml+/−10 ml of inoculated milk preparation.

In order to achieve a pH 4.60, the YOMIX starter needs 375 min and the combination of strains needs 445 min. Both are usual technological times to produce fermented milks at this temperature.

Fresh Fermented Milks Feature Evaluation Methods.

Viscosity of the milk and sensory tasting (texture and flavour attributes) were determined and/or calculated as in example 4.

Results and Comments

The fresh fermented milk features obtained with the co-inoculation of different strains and the commercial culture are reported in Tables 6 and 7.

TABLE 6

Comparison between fresh fermented milks prepared with a blend of DSM 27030/DGCC2057/DGCC10697 and prepared with a commercial culture, YOMIX ™ 465 (YOMIX).

|  | Viscosity (Pa · s) | Relative Breakup Time (ms) |
| --- | --- | --- |
| blend | 62.7 | 60.0 |
| YOMIX | 56.8 | 46.0 |

It can be noticed that the viscosity and the relative break up time of the fresh fermented milk prepared with the blend is significantly higher than the ones measured for the fresh fermented milk prepared with YOMIX.

TABLE 7

Quotation of several sensory attributes for fresh fermented milks prepared with the blend and YOMIX starter cultures.

|  | cut | thickness with spoon | ropiness | thickness in mouth | stickiness | acidity |
| --- | --- | --- | --- | --- | --- | --- |
| blend | 2.0 | 3.0 | 1.5 | 3.5 | 1.0 | 0.0 |
| YOMIX | 3.0 | 2.5 | 0.5 | 2.5 | 1.0 | 0.0 |

For yoghurt prepared with the blend, the "cut" is significantly lower than for the yoghurt prepared with YOMIX. This feature can be of interest for stirred yoghurt production. The "thickness in mouth" is significantly higher for the yoghurt prepared with the blend compared to the yoghurt prepared with YOMIX. This result is valuable for stirred yoghurt technology. Results clearly suggest that strain DSM 27030, combined with other strains, can help yoghurt producers to offer products to the final consumers with very high texture quality.

Therefore, it can be concluded that using DSM 27030 as part of the inoculum provides yoghurt with features of interest for fresh fermented milks producers.

Example 6

Preparation of Fermented Milks Using Strain DSM 27031

Preparation of Fresh Fermented Milks

Fermented milks have been prepared according to example 4, regarding the preparation of milk base and fermentation conditions. The inoculation was performed with strains preserved at −80° C. in milk-based medium. The strain DSM 27031 was combined with a second *Streptococcus thermophilus* strain DGCC2057, and a strain belonging to *Lactobacillus delbrueckii* sub sp. *bulgaricus*, DGCC10697. Inoculation rates were adjusted at $7\times10^5$ CFU/ml, $3\times10^5$ CFU/ml, and $1\times10^4$ CFU/ml of milk-base, respectively. A starter YOMIX™ 465 LYO was used for reference. It was inoculated at commercial dosage of 20 DCU/100 L. Fermentation was carried out in 125 ml yoghurt pot filled with 110 ml+/−10 ml of inoculated milk preparation In order to achieve a pH 4.60, the YOMIX starter needs 375 min and the combination of strains needs 461 min. Both are usual technological times to produce fermented milks at this temperature.

Fresh Fermented Milks Feature Evaluation Methods.

Viscosity of the milk and sensory tasting (texture and flavour attributes) were determined and/or calculated as in example 4.

Fresh Fermented Milks Features

The fresh fermented milk features obtained with the co-inoculation of different strains and the commercial culture are reported in Tables 8 and 9.

TABLE 8

Comparison between fresh fermented milks prepared with a blend of DSM 27031/DGCC2057/DGCC10697 and prepared with a commercial culture, YOMIX ™ 465 (YOMIX).

|  | Viscosity (Pa · s) | Relative Breakup Time (ms) |
|---|---|---|
| blend | 65.2 | 68.0 |
| YOMIX | 56.8 | 46.0 |

It can be noticed that the viscosity and the relative break up time of the fresh fermented milk prepared with the blend is significantly higher than the ones measured for the fresh fermented milk prepared with YOMIX.

TABLE 9

Quotation of several sensory attributes for fresh fermented milk prepared with the blend and YOMIXstarter cultures.

|  | cut | thickness with spoon | ropiness | thickness in mouth | stickiness | acidity |
|---|---|---|---|---|---|---|
| blend | 3.0 | 3.5 | 1.5 | 3.5 | 1.0 | 0.0 |
| YOMIX | 3.0 | 2.5 | 0.5 | 2.5 | 1.0 | 0.0 |

The "thickness in spoon" and the "thickness in mouth" are noticeably higher for yoghurt prepared with the blend as compared to the yoghurt prepared with YOMIX. This result is valuable for stirred yoghurt technology. Results clearly suggest that strain DSM27031, combined with other strains, can help yoghurt producers to offer products to the final consumers with very high texture quality.

Therefore, it can be concluded that using DSM 27031 as part of the inoculum provides yoghurt with features of interest for fresh fermented milks producers.

Example 7

Preparation of Fermented Milks Using Strain DSM 27031 and Comparison with Other *Streptococcus thermophilus* Strains Preparation of Fermented Milks Fermented milks were prepared according to example 4, regarding the preparation of milk base and fermentation conditions. Two mixed cultures were prepared: formula A containing *Streptococcus thermophilus* strains DGCC8897 and DSM 27031, and *Lactobacillus delbrueckii bulgaricus* strain DGCC10697, and formula B containing *Streptococcus thermophilus* strains DGCC8897 and DGCC7891, and *Lactobacillus delbrueckii bulgaricus* strain DGCC10697. The inoculation was performed with strains preserved at −80° C. in milk-based medium. The inoculation rates for mixed culture A and mixed culture B, and the S1 and S2 values of each used *Streptococcus thermophilus* strain are reported in Table 10. In formula B, strain DGCC7891 was chosen as a reference example, because it has a high S2/S1 ratio (39%) as compared to strain DSM 27031 (16%).

TABLE 10

Inoculation rate in CFU/ml for mixed cultures tests named Formula A and formula B, and $S_1$, $S_2$ and $S_2/S_1$ values for the *Streptococcus thermophilus* strains used.

|  | *Streptococcus thermophilus* DGCC8897 | *Streptococcus thermophilus* DGCC7891 | *Streptococcus thermophilus* DSM 27031 | *Lactobacillus delbrueckii bulgaricus* DGCC10697 |
|---|---|---|---|---|
| Formula A | $8.10^5$ | — | $2.10^5$ | $1.10^4$ |
| Formula B | $8.10^5$ | $2.10^5$ | — | $1.10^4$ |
| $S_1$ ($10^{-4}$ UpH/min) | 139 | 34 | 98 | / |
| $S_2$ ($10^{-4}$ UpH/min) | 72 | 13 | 16 | / |
| S2/S1 (%) | 52 | 39 | 16 | / |

Fermentation were carried out in 125 ml yoghurt pot filled with 110 ml+/−10 ml of inoculated milk preparation In order to achieve a pH 4.60, formula B needed 300 min, and formula A needed 440 min. Both are usual technological times to produce fermented milks at this temperature.

Fresh Fermented Milks Feature Evaluation Methods.

Viscosity of the milk and sensory tasting (texture and flavour attributes) were determined and/or calculated as in example 4.

pH Evolution During Storage

At pH 4.60+/−0.1, the fermented product was cooled down to 6° C., and then stored at 6° C. for 50 days. The pH of the fermented milks obtained with formula A or with formula B stored at 6° C. has been measured after 14 days, 28 days, and 50 days.

Results and Comments

The fresh fermented milk features obtained with the co-inoculation of different strains (formula A or B) are reported in Tables 11 and 12.

TABLE 11

Comparison between fresh fermented milks prepared with formula A and formula B.

|  | Viscosity (Pa · s) | Relative Breakup Time (ms) | pH (14 days at 6° C.) | pH (28 days at 6° C.) | pH (50 days at 6° C.) |
|---|---|---|---|---|---|
| Formula A | 42.0 | 8.0 | 4.42 | 4.40 | 4.39 |
| Formula B | 35.2 | 21.0 | 4.35 | 4.34 | 4.33 |

It can be noticed that the viscosity of the fresh fermented milk A is significantly higher than fresh fermented milk B, meaning potentially a higher global texture development in the yoghurt. Furthermore, the relative break up time of yoghurt prepared with formula A is markedly lower than the one of fermented milk done with formula B. This can be an indication of less ropiness development for this product. It is also noteworthy that the pH value of the yoghurt prepared with formula A (i.e., containing one strain according to the invention) is significantly higher than the pH of the yoghurt prepared with formula B (i.e., without a strain according to the invention), during the total duration of storage of the yoghurt at 6° C. (at days 14, 28 and 50). Interestingly, the pH of the yoghurt prepared with formula A is more than 4.40 when stored 14 days at 6° C., whereas the pH of the yoghurt prepared with formula B is 4.35.

TABLE 12

Quotation of several sensory attributes for fresh fermented milk obtained with formula A or formula B.

|  | cut | thickness with spoon | ropiness | thickness in mouth | stickiness | acidity |
|---|---|---|---|---|---|---|
| Formula A | 4 | 2 | 0 | 1 | 0 | 0 |
| Formula B | 3 | 2 | 0.5 | 1 | 0.5 | 0 |

The "ropiness" and the "stickiness in mouth" of formula A prepared with DSM 27031 is less important than for formula B. This result is valuable for stirred yoghurt technology.

Results clearly suggest that strain DSM 27031, combined with other strains, can help yoghurt producers to offer products to the final consumers with high texture quality and very mild taste.

Example 8

Preparation of Fermented Milks Using Strain DSM 27029 and Comparison with *Streptococcus thermophilus* Strains Preparation of Fermented Milks Using Strain DSM 27029

Fermented milks were prepared according to example 4, regarding the preparation of milk base and fermentation conditions. Two mixed cultures were prepared: formula C containing *Streptococcus thermophilus* strains DGCC938 and DSM 27029, and *Lactobacillus delbrueckii bulgaricus* strain DGCC10697, and formula D containing *Streptococcus thermophilus* strains DGCC8897 and DGCC938, and *Lactobacillus delbrueckii bulgaricus* strain DGCC10697. The inoculation was performed with strains preserved at −80° C. in milk-based medium. The inoculation rates for mixed culture C and mixed culture D, and the S1 and S2 values of each used *Streptococcus thermophilus* strain are reported in Table 13.

TABLE 13

Inoculation rate for mixed cultures tests named Formula C and formula D, and $S_1$, $S_2$ and $S_2/S_1$ values for the *Streptococcus thermophilus* strains used.

|  | Streptococcus thermophilus DGCC8897 | Streptococcus thermophilus DGCC938 | Streptococcus thermophilus DSM 27029 | Lactobacillus delbrueckii bulgaricus DGCC10697 |
|---|---|---|---|---|
| Formula C | — | $1.10^6$ | $3.10^6$ | $8.10^3$ |
| Formula D | $2.10^6$ | $1.10^6$ | — | $8.10^4$ |
| $S_1$ ($10^{-4}$ UpH/min) | 139 | 40 | 98 | / |
| $S_2$ ($10^{-4}$ UpH/min) | 72 | 15 | 11 | / |
| S2/S1 (%) | 52 | 38 | 11 | / |

Fermentation were carried out in 125 ml yoghurt pot filled with 110 ml+/−10 ml of inoculated milk preparation.

In order to achieve a pH 4.60 (time at which the product is cooled down from 43° C. to 6° C.), the fermentation of milk inoculated with formula C took 370 min, and 389 min for formula D Both are usual technological times to produce fermented milks at this temperature.

Fresh Fermented Milks Feature Evaluation Methods.

Viscosity of the milk and sensory tasting (texture and flavour attributes) were determined and/or calculated as in example 4.

pH Evolution During Storage

The pH of the fermented milks obtained with formula C or with formula D stored at 6° C. has been measured after 14 days, 28 days, and 50 days.

Results and Comments

The fresh fermented milk features obtained with the co-inoculation of different strains (formula C or D) are reported in Tables 14 and 15.

TABLE 14

Comparison between fresh fermented milks prepared with formula C and formula D.

| | Viscosity (Pa · s) | Relative Breakup Time (ms) | pH (14 days at 6° C.) | pH (28 days at 6° C.) | pH (50 days at 6° C.) |
|---|---|---|---|---|---|
| Formula C | 55.9 | 57.6 | 4.57 | 4.50 | 4.40 |
| Formula D | 34.8 | 11.8 | 4.39 | 4.37 | 4.39 |

It can be noticed that the viscosity of the fresh fermented milk C is significantly higher than fresh fermented milk D, meaning potentially a higher global texture development in the yoghurt.

It is also noteworthy that the pH value of the yoghurt prepared with formula C (i.e., containing one strain according to the invention) is significantly higher than the pH of the yoghurt prepared with formula D (i.e., without a strain according to the invention), until 28 days of storage. Interestingly, the pH of the yoghurt prepared with formula C is about 4.50 when stored 28 days at 6° C., whereas the pH of the yoghurt prepared with formula D is 4.37.

TABLE 15

Quotation of several sensory attributes for fresh fermented milk obtained with formula C or formula D.

| | cut | thickness with spoon | ropiness | thickness in mouth | acidity |
|---|---|---|---|---|---|
| Formula C | 2.5 | 4 | 1.5 | 4 | 0 |
| Formula D | 4 | 1 | 0 | 1 | 0 |

The "thickness with spoon" and the "thickness in mouth" of formula C prepared with DSM 27029 is more important than for formula D. This result is valuable for stirred yoghurt technology. Results clearly suggest that strain DSM 27029, combined with other strains, can help yoghurt producers to offer products to the final consumers with high texture quality and very mild taste.

---

The invention claimed is:

1. A composition comprising a *Streptococcus thermophilus* strain and a food acceptable component, wherein:
   the food acceptable component is selected from cryoprotective agents and boosters;
   the *Streptococcus thermophilus* strain exhibits milk acidification kinetics characterized as follows:
   (1) an average speed of acidification between pH 6.00 and pH 5.30 which is at least $70 \times 10^{-4}$ UpH/min, and
   (2) an average speed of acidification between pH 5.30 and pH 5.00 which is no greater than $22 \times 10^{-4}$ UpH/min; and
   the average speeds of acidification of (1) and (2) are measured under the following conditions:
   ultra high-temperature pasteurized cow-milk milk having a fat content of fat 1.5% (w/w) is supplemented with 3% (w/w) skimmed milk powder to form a mixture at a temperature of from 20 to 25° C.;
   after the powder dissolves, the mixture is heated to 90° C. over a period of no greater than 35 minutes;
   the mixture is maintained at 90° C. for 10 minutes and then cooled to 35° C.-45° C. over a period of no greater than 45 minutes;
   1 g/100 L of sodium formate is added to the mixture;
   the mixture is inoculated with the *Streptococcus thermophilus* strain, wherein:
   the *Streptococcus thermophilus* strain is in a preserved form at −80° C. in a milk-based medium, and
   the inoculation rate is $1 \times 10^6$ CFU/ml of the milk-base medium; and
   the inoculated mixture is incubated at a temperature of 43° C. (+/−1° C.), which is kept constant in a water bath, while measuring change in pH every 5 minutes for 24 hours.

2. The composition of claim 1, wherein the *Streptococcus thermophilus* strain is selected from the group consisting of:
   (1) the DSM 27029 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (2) the DSM 27030 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (3) the DSM 27031 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH; and
   (4) a mutant strain having all of the identifying characteristics of the DSM 27029 strain, of the DSM 27030 strain, or of the DSM 27031 strain.

3. A composition comprising a *Streptococcus thermophilus* strain, wherein:
   the composition is in a liquid, frozen or dried-powder form;
   the *Streptococcus thermophilus* strain exhibits milk acidification kinetics characterized as follows:
   (1) an average speed of acidification between pH 6.00 and pH 5.30 which is at least $70 \times 10^{-4}$ UpH/min, and
   (2) an average speed of acidification between pH 5.30 and pH 5.00 which is no greater than $22 \times 10^{-4}$ UpH/min; and
   the average speeds of acidification of (1) and (2) are measured under the following conditions:
   ultra high-temperature pasteurized cow-milk milk having a fat content of fat 1.5% (w/w) is supplemented with 3% (w/w) skimmed milk powder to form a mixture at a temperature of from 20 to 25° C.;
   after the powder dissolves, the mixture is heated to 90° C. over a period of no greater than 35 minutes;
   the mixture is maintained at 90° C. for 10 minutes and then cooled to 35° C.-45° C. over a period of no greater than 45 minutes;
   1 g/100 L of sodium formate is added to the mixture;
   the mixture is inoculated with the *Streptococcus thermophilus* strain, wherein:
   the *Streptococcus thermophilus* strain is in a preserved form at −80° C. in a milk-based medium, and
   the inoculation rate is $1 \times 10^6$ CFU/ml of the milk-base medium; and
   the inoculated mixture is incubated at a temperature of 43° C. (+/−1° C.), which is kept constant in a water bath, while measuring change in pH every 5 minutes for 24 hours.

4. The composition of claim 3, wherein the composition is in a frozen form.

5. The composition of claim 3, wherein the composition is in a freeze-dried powder form.

6. The composition of claim 3, wherein the *Streptococcus thermophilus* strain is selected from the group consisting of:
   (1) the DSM 27029 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (2) the DSM 27030 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (3) the DSM 27031 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH; and
   (4) a mutant strain having all of the identifying characteristics of the DSM 27029 strain, of the DSM 27030 strain, or of the DSM 27031 strain.

7. A method for preparing a food or a feed product comprising:
   putting into contact a substrate with a culture of a *Streptococcus thermophilus* strain; and
   obtaining the product, wherein:
   the substrate comprises pasteurized milk;
   the *Streptococcus thermophilus* strain exhibits milk acidification kinetics characterized as follows:
   (1) an average speed of acidification between pH 6.00 and pH 5.30 which is at least $70 \times 10^{-4}$ UpH/min, and
   (2) an average speed of acidification between pH 5.30 and pH 5.00 which is no greater than $22 \times 10^{-4}$ UpH/min; and
   the average speeds of acidification of (1) and (2) are measured under the following conditions:
   ultra high-temperature pasteurized cow-milk milk having a fat content of fat 1.5% (w/w) is supplemented with 3% (w/w) skimmed milk powder to form a mixture at a temperature of from 20 to 25° C.;
   after the powder dissolves, the mixture is heated to 90° C. over a period of no greater than 35 minutes;
   the mixture is maintained at 90° C. for 10 minutes and then cooled to 35° C.-45° C. over a period of no greater than 45 minutes;
   1 g/100 L of sodium formate is added to the mixture;
   the mixture is inoculated with the *Streptococcus thermophilus* strain, wherein:
   the *Streptococcus thermophilus* strain is in a preserved form at −80° C. in a milk-based medium, and
   the inoculation rate is $1 \times 10^6$ CFU/ml of the milk-base medium; and
   the inoculated mixture is incubated at a temperature of 43° C. (+/−1° C.), which is kept constant in a water bath, while measuring change in pH every 5 minutes for 24 hours.

8. The method according to claim 7, wherein the milk acidification kinetics of the strain are characterized by a ratio of the (1) average speed of acidification between pH 5.30 and pH 5.00 to the (2) average speed of acidification between pH 6.00 and pH 5.30 being less than or equals 25%.

9. The method according to claim 8, wherein the milk acidification kinetics of the *Streptococcus thermophilus* strain are characterized by a ratio of the (1) average speed of acidification between pH 5.30 and pH 5.00 to the (2) average speed of acidification between pH 6.00 and pH 5.30 being between 2 and 25%.

10. The method according to claim 7, wherein the genome of the *Streptococcus thermophilus* strain comprises a) a CRISPR4 locus comprising or consisting of the sequence as defined in SEQ ID NO:3 orb) a CRISPR4 locus comprising part(s) of SEQ ID NO:3.

11. The method according to claim 7, wherein the genome of the *Streptococcus thermophilus* strain comprises a) a CRISPR1 locus consisting of SEQ ID NO:19, orb) a CRISPR1 locus comprising SEQ ID NO:19 or comprising part(s) of SEQ ID NO:19, and optionally additional CRISPR1 [repeat-spacer] unit(s) of sequence R1-X1, wherein R1 is as defined in SEQ ID NO:20, and X1 is any sequence with a length of from 27 to 33 bp.

12. The method according to claim 7, wherein the genome of the *Streptococcus thermophilus* strain comprises a) a CRISPR3 locus consisting of SEQ ID NO:73, or b) a CRISPR3 locus comprising SEQ ID NO:73 or comprising part(s) of SEQ ID NO:73, and optionally additional CRISPR3 [repeat-spacer] unit(s) of sequence R3-X3, wherein R3 is as defined in SEQ ID NO:74, and X3 is any sequence with a length from 27 to 33 bp.

13. The method according to claim 7, wherein the *Streptococcus thermophilus* strain exhibits milk acidification kinetics characterized as follows:
   the (1) average speed of acidification between pH 6.00 and pH 5.30 is between $70 \times 10^{-4}$ and $250 \times 10^{-4}$; and
   the (2) average speed of acidification between pH 5.30 and pH 5.00 is between $1 \times 10^{-4}$ and $20 \times 10'$.

14. The method according claim 7, wherein a composition comprising the *Streptococcus thermophilus* strain and at least one other microorganism is contacted with the substrate.

15. The method according to claim 14, wherein:
   the at least one other microorganism comprises a lactic acid bacterium; and
   the lactic acid bacterium is selected from:
   a different strain of the species *Streptococcus thermophilus*,
   a strain of the subspecies *Lactobacillus delbrueckii* subsp. *bulgaricus*, and
   a strain of the genus *Bifidobacterium*.

16. The method according to claim 7, wherein the *Streptococcus thermophilus* strain is selected from the group consisting of:
   (1) the DSM 27029 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (2) the DSM 27030 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (3) the DSM 27031 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH; and
   (4) a mutant strain having all of the identifying characteristics of the DSM 27029 strain, of the DSM 27030 strain, or of the DSM 27031 strain.

17. A food or a feed product prepared by the method of claim 16.

18. The food or feed product according to claim 17, wherein the product comprises a fermented dairy food.

19. The food or feed product according to claim 17, wherein the product is selected from the group consisting of a yogurt, cheese, buttermilk, quark, sour cream, kefir, fermented whey-based beverage, koumiss, milk beverage, yoghurt drink, fermented milk, matured cream, fromage frais, milk, dairy product retentate, processed cheese, cottage cheese, cream dessert, and infant milk.

20. A method for preparing a food or a feed product comprising:
putting into contact a substrate with composition comprising a culture of a *Streptococcus thermophilus* strain; and
obtaining the product, wherein:
the composition further comprises a food acceptable component;
the food acceptable component is selected from cryoprotective agents, boosters, yeast extracts, sugars and vitamins;
the *Streptococcus thermophilus* strain exhibits milk acidification kinetics characterized as follows:
(1) an average speed of acidification between pH 6.00 and pH 5.30 which is at least $70 \times 10^{-4}$ UpH/min, and
(2) an average speed of acidification between pH 5.30 and pH 5.00 which is no greater than $22 \times 10^{-4}$ UpH/min; and
the average speeds of acidification of (1) and (2) are measured under the following conditions:
ultra high-temperature pasteurized cow-milk milk having a fat content of fat 1.5% (w/w) is supplemented with 3% (w/w) skimmed milk powder to form a mixture at a temperature of from 20 to 25° C.;
after the powder dissolves, the mixture is heated to 90° C. over a period of no greater than 35 minutes;
the mixture is maintained at 90° C. for 10 minutes and then cooled to 35° C.-45° C. over a period of no greater than 45 minutes;
1 g/100 L of sodium formate is added to the mixture;
the mixture is inoculated with the *Streptococcus thermophilus* strain, wherein:
the *Streptococcus thermophilus* strain is in a preserved form at −80° C. in a milk-based medium, and
the inoculation rate is $1 \times 10^6$ CFU/ml of the milk-base medium; and
the inoculated mixture is incubated at a temperature of 43° C. (+/−1° C.), which is kept constant in a water bath, while measuring change in pH every 5 minutes for 24 hours.

21. The method according to claim 20, wherein the substrate comprises milk.

22. The method according to claim 20, wherein the substrate comprises pasteurized milk.

23. The method according to claim 20, wherein the composition is in a liquid, frozen, or freeze-dried powder form.

24. The method of claim 20, wherein the *Streptococcus thermophilus* strain is selected from the group consisting of:
(1) the DSM 27029 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
(2) the DSM 27030 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
(3) the DSM 27031 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH; and
(4) a mutant strain having all of the identifying characteristics of the DSM 27029 strain, of the DSM 27030 strain, or of the DSM 27031 strain.

25. A food or feed product prepared by the method of claim 24, wherein the food or feed product is a dairy food or feed product.

26. The food or feed product according to claim 25, wherein the product is selected from the group consisting of a yogurt, cheese, buttermilk, quark, sour cream, kefir, fermented whey-based beverage, koumiss, milk beverage, yoghurt drink, fermented milk, matured cream, fromage frais, milk, dairy product retentate, processed cheese, cottage cheese, cream dessert, and infant milk.

27. A method for preparing a food or a feed product comprising:
putting into contact a substrate with composition comprising a culture of a *Streptococcus thermophilus* strain; and
obtaining the product, wherein:
the composition is in a liquid, frozen or dried-powder form;
the *Streptococcus thermophilus* strain exhibits milk acidification kinetics characterized as follows:
(1) an average speed of acidification between pH 6.00 and pH 5.30 which is at least $70 \times 10^{-4}$ UpH/min, and
(2) an average speed of acidification between pH 5.30 and pH 5.00 which is no greater than $22 \times 10^{-4}$ UpH/min; and
the average speeds of acidification of (1) and (2) are measured under the following conditions:
ultra high-temperature pasteurized cow-milk milk having a fat content of fat 1.5% (w/w) is supplemented with 3% (w/w) skimmed milk powder to form a mixture at a temperature of from 20 to 25° C.;
after the powder dissolves, the mixture is heated to 90° C. over a period of no greater than 35 minutes;
the mixture is maintained at 90° C. for 10 minutes and then cooled to 35° C.-45° C. over a period of no greater than 45 minutes;
1 g/100 L of sodium formate is added to the mixture;
the mixture is inoculated with the *Streptococcus thermophilus* strain, wherein:
the *Streptococcus thermophilus* strain is in a preserved form at −80° C. in a milk-based medium, and
the inoculation rate is $1 \times 10^6$ CFU/ml of the milk-base medium; and
the inoculated mixture is incubated at a temperature of 43° C. (+/−1° C.), which is kept constant in a water bath, while measuring change in pH every 5 minutes for 24 hours.

28. The method of claim 27, wherein the composition is in a frozen form.

29. The method of claim 27, wherein the composition is in a freeze-dried powder form.

30. The method according to claim 27, wherein the substrate comprises milk.

31. The method according to claim 27, wherein the substrate comprises pasteurized milk.

32. The method of claim 27, wherein the *Streptococcus thermophilus* strain is selected from the group consisting of:
   (1) the DSM 27029 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (2) the DSM 27030 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH;
   (3) the DSM 27031 strain, deposited under the Budapest Treaty on Mar. 21, 2013 in the name of Danisco Deutschland GmbH at the Leibniz-Institut DSMZ-Deutsche Sammlung von Mikroorganismen und Zellkulturen, GmbH; and
   (4) a mutant strain having all of the identifying characteristics of the DSM 27029 strain, of the DSM 27030 strain, or of the DSM 27031 strain.

33. A food or feed product prepared by the method of claim 32, wherein the food or feed product is a dairy food or feed product.

34. The food or feed product according to claim 33, wherein the product is selected from the group consisting of a yogurt, cheese, buttermilk, quark, sour cream, kefir, fermented whey-based beverage, koumiss, milk beverage, yoghurt drink, fermented milk, matured cream, fromage frais, milk, dairy product retentate, processed cheese, cottage cheese, cream dessert, and infant milk.

\* \* \* \* \*